(12) United States Patent
Ryan et al.

(10) Patent No.: US 10,130,473 B2
(45) Date of Patent: *Nov. 20, 2018

(54) ANNULOPLASTY DEVICE FOR TRICUSPID VALVE REPAIR

(71) Applicant: Medtronic, Inc., Minneapolis, MN (US)

(72) Inventors: Timothy R. Ryan, Minnetrista, MN (US); Alexander J. Hill, Blaine, MN (US); Jason L. Quill, Forest Lake, MN (US); Jerald L. Redmond, Germantown, TN (US); Stephen Kuehn, Woodbury, MN (US); Eugene Grossi, New York, NY (US); Aubrey Galloway, Bronxville, NY (US); Hugo Vanermen, Aalst (BE); Rudiger Lange, Munich (DE)

(73) Assignee: Medtronic, Inc., Minneapolis, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/712,575

(22) Filed: Sep. 22, 2017

(65) Prior Publication Data

US 2018/0008411 A1 Jan. 11, 2018

Related U.S. Application Data

(63) Continuation of application No. 15/200,929, filed on Jul. 1, 2016, now Pat. No. 9,801,718, which is a
(Continued)

(51) Int. Cl.
*A61F 2/24* (2006.01)
*A61B 17/06* (2006.01)

(52) U.S. Cl.
CPC .......... *A61F 2/2445* (2013.01); *A61F 2/2448* (2013.01); *A61B 17/06066* (2013.01); *A61F 2230/0013* (2013.01)

(58) Field of Classification Search
CPC .... A61F 2/2445; A61F 2/2466; A61F 2/2448; A61F 2/2454
See application file for complete search history.

(56) References Cited

U.S. PATENT DOCUMENTS

| 5,104,407 A | 4/1992 | Lam et al. |
| 5,824,066 A | 10/1998 | Gross |

(Continued)

FOREIGN PATENT DOCUMENTS

| EP | 1 034 753 | 9/2000 |
| WO | 00/74603 | 12/2000 |

(Continued)

OTHER PUBLICATIONS

Antunes et al., "DeVega Annuloplasty of the Tricuspid Valve," Operative Techniques in Thoracic and Cardiovascular Surgery, Nov.; 8(4):169-176 (2003).
(Continued)

*Primary Examiner* — Thomas J Sweet
*Assistant Examiner* — Tiffany Shipmon
(74) *Attorney, Agent, or Firm* — Dicke, Billig & Czaja, PLLC

(57) ABSTRACT

Annuloplasty device for implantation adjacent an annulus of a tricuspid valve, the annulus comprising anterior, posterior and septal aspects adjacent anterior, posterior and septal leaflets, respectively, of the tricuspid valve, the device comprising: a ring body comprising: an anterior portion, a posterior portion and a septal portion shaped to conform to, and for implantation adjacent, the anterior, posterior and septal aspects of the annulus, respectively; and first and
(Continued)

second end portions that are more flexible than a remainder of the ring body to provide a gradual transition from the remainder of the ring body to tissue of the tricuspid valve annulus; wherein the ring body is curvilinear, with substantially no flat portions, and forming a shape. Related devices, kits and sizer devices.

10 Claims, 19 Drawing Sheets

Related U.S. Application Data continuation of application No. 12/847,655, filed on Jul. 30, 2010, now Pat. No. 9,381,084, which is a continuation-in-part of application No. 12/011,482, filed on Jan. 25, 2008, now Pat. No. 8,535,374.

(60) Provisional application No. 60/897,696, filed on Jan. 26, 2007.

(56) References Cited

U.S. PATENT DOCUMENTS

| | | |
|---|---|---|
| 6,749,630 B2 | 6/2004 | McCarthy et al. |
| 6,786,924 B2 | 9/2004 | Ryan et al. |
| 6,805,710 B2 | 10/2004 | Bolling et al. |
| 6,858,039 B2 | 2/2005 | McCarthy |
| 2001/0049557 A1 | 12/2001 | Chinn et al. |
| 2003/0093148 A1 | 5/2003 | Bolling et al. |
| 2003/0208264 A1 | 11/2003 | McCarthy et al. |
| 2004/0138744 A1 | 7/2004 | Lashinski et al. |
| 2005/0004669 A1 | 1/2005 | Sievers |
| 2005/0021135 A1 | 1/2005 | Ryan |
| 2005/0043791 A1 | 2/2005 | McCarthy et al. |
| 2005/0256568 A1 | 11/2005 | Lim et al. |
| 2005/0288776 A1 | 12/2005 | Shaoulian et al. |
| 2005/0288778 A1 | 12/2005 | Shaoulian et al. |
| 2006/0025856 A1 | 2/2006 | Ryan et al. |
| 2006/0129236 A1 | 6/2006 | McCarthy |
| 2006/0265056 A1 | 11/2006 | Nguyen et al. |
| 2007/0239266 A1 | 10/2007 | Birdsall |
| 2007/0239269 A1 | 10/2007 | Dolan et al. |

FOREIGN PATENT DOCUMENTS

| | | |
|---|---|---|
| WO | 03/020178 | 3/2003 |
| WO | 05/112830 | 12/2005 |
| WO | 06/102513 | 9/2006 |
| WO | 08/011261 | 1/2008 |

OTHER PUBLICATIONS

Babaliaros, V.C., et al., "Can Balloon Aortic Valvuloplasty Help Determine Appropriate Transcatheter Aortic Valve Size", JAAC, 2008, vol. 1, No. 5, pp. 580-586.

Bashore, T.M. et al., "Percutaneous Balloon Aortic Valvuloplasty," Circulation, 1991, vol. 84, No. 6, pp. 2383-2397.

Carpentier et al., "Surgical management of acquired tricuspid valve disease," Journal of Thoracic Cardiovascular Surgeon, 67(1):53-65 (1974).

Carpentier-Edwards Classic Annuloplasty Rings, Edwards Lifesciences (2003), 2 pages.

Dwork, J. et al., U.S. Appl. No. 61/237,373, filed Aug. 27, 2009, now relating to U.S. Appl. No. 12/870,567.

Ferguson, J.J., III et al. "Balloon Aortic Valvuloplasty" Texas Heart Institute Journal 1990; 17:23-30.

Filsoufi, et al., "Surgical Management of Functional Tricuspid Regurgitation with a New Remodeling Annuloplasty Ring," Mount Sinai Journal of Medicine, vol. 73, No. 6, Oct. 2006, pp. 874-879.

Fukuda et al., "Three Dimensional Geometry of the Tricuspid Annulus in Healthy Subjects and in Patients with Functional Tricuspid Regurgitation: A Real-Time, 3-Dimensional Echocardiographic Study," Circulation, 114 (I Suppl) 1492-8 (2006).

Gorman, et al., "The Effect of Regional ischemia on Mitral Valve Annular Saddle Shape," Society of Thoracic Surgeons, 2004;77:544-8.

Hiro et al., "Sonometric Study of the Normal Tricuspid Valve Annulus in Sheep," The Journal of Heart Valve Disease, 13(3):452-460 (2004).

Manuel J. Antunes, "DeVega Annuloplasty of the Tricuspid Valve," Operative Techniques in Thoracic and Cardiovascular Surgery, vol. 8, No. 4, Nov. 2003, pp. 169-176.

McGuire, et al., "Dimensions of the Triangle of Koch in Humans," The American Journal of Cardiology, vol. 70, Sep. 15, 2992, pp. 829-830.

Medtronic, "A Patients Guide to Heart Valve Surgery," 2004.

Minale et al., "New Developments for Reconstruction of the Tricuspid Valve," J. Thorac. Cardiovas. Surg., Oct.; 94(4):626-31 (1987).

Raffoul, et al., "Clinical Evaluation of the Physio Annuloplasty Ring," CHEST, 1998;113; 1296-1301.

Salgo, et al., "Effect of Annular shape on Leaflet Curvature in Reducing Mitral Leaflet Stress," Circulation, Aug. 6, 2002, pp. 711-717.

Sharony et al., "Repair of Tricuspid Regurgitation: The Posterior Annuloplasty Technique," Operative Techniques in Thoracic and Cardiovascular Surgery, Nov.; 8(4):177-183 (2003).

Timek, et al., "Annular Height-to-Commissural Width Ratio of Annuloplasty Rings in Vivo," Circulation, Aug. 30, 2005, pp. I-423-I-428.

Ton-Nu et al., "Geometric Determinants of Functional Tricuspid Regurgitation: Insights From 3-Dimensional Echocardiography," Circulation, 114:143-149 (2006).

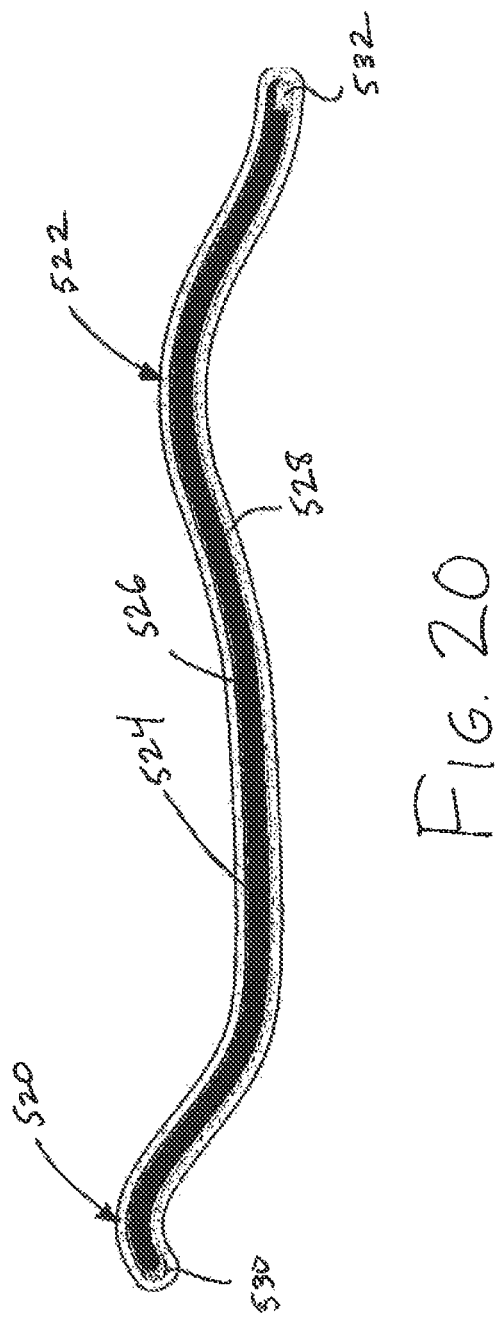

ANNULOPLASTY DEVICE FOR TRICUSPID VALVE REPAIR

CROSS REFERENCE TO RELATED APPLICATION

The present application is a continuation of U.S. Ser. No. 15/200,929, filed Jul. 1, 2016, now allowed, which is a continuation of U.S. Ser. No. 12/847,655, filed Jul. 30, 2010, now U.S. Pat. No. 9,381,084, which is a continuation in part of U.S. Ser. No. 12/011,482, filed Jan. 25, 2008, now U.S. Pat. No. 8,535,374, which is the nonprovisional application claiming priority to Provisional Application Ser. No. 60/897,696, filed Jan. 26, 2007, the entire contents of each of which are fully incorporated herein by reference.

TECHNICAL FIELD

The present invention relates generally to devices and methods for repair of heart valves, and more particularly to an annuloplasty device having two-dimensional (2D) and/or three-dimensional (3D) shape that either mimics a healthy, native tricuspid valve annulus in shape or otherwise restores the annular shape of an incompetent tricuspid valve annulus to a shape more closely representing the 3D shape of a healthy, native tricuspid valve.

BACKGROUND OF THE INVENTION

Heart valve disease is a widespread condition in which one or more of the valves of the heart fails to function properly. Various surgical techniques may be used to replace or repair a diseased or damaged valve. In just one way, in a valve replacement surgery, damaged leaflets of the valve are excised and the annulus is sculpted to receive a replacement valve. Another less drastic method for treating defective valves is repair or reconstruction by annuloplasty, in which the effective size of the valve annulus is contracted and reinforced, by attaching a prosthetic annuloplasty repair segment or ring to an interior wall of the heart around the valve annulus. The annuloplasty ring is designed to support the functional changes that occur during the cardiac cycle; maintaining coaptation and valve integrity.

One of the two atrio-ventricular valves in the heart is the tricuspid valve. The tricuspid valve regulates blood flow between the right atrium and the right ventricle. Anatomically speaking, the tricuspid valve 10, as seen in FIG. 1, includes an annulus 12 that is the portion of the wall of the heart where three valve leaflets 14, 16, 18 (septal, anterior, and posterior, respectively) insert into the heart wall tissue. The leaflets 14, 16, 18 extend inward into the valve or flow orifice defined by the annulus 12. There are three commissures between the three leaflets, which include an anteroseptal commissure 20, a posteroseptal commissure 22 and an anteroposterior commissure 24. Chordae tendinae 26 connect the leaflets to papillary muscles located in the right ventricle to control the movement of the leaflets. The tricuspid annulus 12 is an ovoid-shaped structure ring at the base of the valve. The annulus 12 has contractile function and can change shape throughout a cardiac cycle. The portions of the tricuspid valve annulus 12 that are attached to the septal 14, anterior 16 and posterior 18 leaflets are called the septal 34, anterior 36 and posterior 38 aspects, respectively. The anterior and posterior leaflets are also known, respectively, as the anterosuperior and inferior leaflets. Similarly, the aspects of the annulus may be referred to using these alternative terms.

With particular regard to the tricuspid valve, the primary dysfunction is dilation of the anterior and posterior aspects of the valve annulus. Annulus dilation can lead to incomplete leaflet coaptation, causing a condition known as tricuspid regurgitation. Studies have shown that the posterior aspect can be dilated as much as 80% of its original length, whereas the anterior aspect can be dilated by as much as 40% (Carpentier et al. (1974), Surgical management of acquired tricuspid valve disease, *Journal of the Thoracic Cardiovascular Surgeon,* 67(1): 53-65). The septal aspect of the annulus lies along the atrioventricular septum of the heart and does not dilate as much as the other aspects (typically 10% or less of its original length).

Consequently, when a tricuspid valve is repaired surgically, the goal is to reduce the size of and reinforce one or both of the anterior and posterior aspects of the valve annulus. Early methods used to reduce the size of the anterior and/or posterior aspects were suture-based. One method called "bicuspidization" used sutures to effectively eliminate the posterior leaflet, and is described in Sharony et al. (2003), Repair of Tricuspid Regurgitation: The Posterior Annuloplasty Technique, *Operative Techniques in Thoracic and Cardiovascular Surgery,* November; 8(4): 177-183. Another method called "sliding plasty" involves separation of the leaflets from the annulus, plication/shortening of the annulus, and reattachments of the leaflets, and is described in Minale et al. (1987), New Developments for Reconstruction of the Tricuspid Valve, *J. Thorac. Cardiovasc. Surg.,* October; 94(4): 626-31. Yet another method used, called the "modified DeVega tricuspid annuloplasty," involves placing a suture or series of sutures around the annulus and pulling the sutures tight to reduce the perimeter of the annulus, as described in Antunes et al. (2003), DeVega Annuloplasty of the Tricuspid Valve, *Operative Techniques in Thoracic and Cardiovascular Surgery,* November; 8(4): 169-176.

One current method used to reduce the tricuspid valve annulus is remodeling annuloplasty. Remodeling annuloplasty involves implanting a prosthetic ring or band in a supra annular position. The purpose of the ring or band is to restrict and/or support an annulus to correct and/or prevent valvular insufficiency. Remodeling annuloplasty is an important part of surgical valve repair. Three objectives of surgical valve repair include: 1) restore large surface of leaflet coaptation; 2) preserve leaflet mobility; and 3) stabilize the annulus and avoid further dilatation. In remodeling annuloplasty, both annuloplasty rings and annuloplasty bands are used for repair of valves. In general terms, annuloplasty rings completely encompass a valve annulus, while annuloplasty bands are designed to primarily encompass only a portion of the valve annulus. Examples of annuloplasty bands are shown in U.S. Pat. Nos. 5,824,066, and 6,786,924, and PCT International Patent Publication No. WO00/74603, the teachings of which are incorporated herein by reference.

Annuloplasty surgery associated with the tricuspid valve is generally intended to restore normal leaflet coaptation by reversing annulus dilation through plication. A way to restore leaflet coaptation is to restore the annulus to its normal or native shape during ventricular contraction or systole. However, the shape of the tricuspid annulus during portions of the cardiac cycle has not been well defined. Recent publications provide evidence that the tricuspid valve annulus has a nonplanar or 3D structure, which is described as "saddle-shaped," and undergoes complex geometric changes during the cardiac cycle. (See, Fukuda et al. (2006), Three Dimensional Geometry of the Tricuspid Annulus in Healthy Subjects and in Patients with Functional Tricuspid Regurgitation: A Real-Time, 3-Dimensional Echocardiographic Study, *Circulation,* 114: 492-498; Ton-Nu et al. (2006), Geometric Determinants of Functional Tricuspid Regurgitation: Insights From 3-Dimensional Echocardiography, *Circulation,* 114: 143-149; Hiro et al. (2004), Sonometric Study of the Normal Tricuspid Valve Annulus in Sheep, *The Journal of Heart Valve Disease,* 13(1): 452-460).

In close proximity to the tricuspid valve is the atrioventricular (AV) node 28 (FIG. 1). The AV node is a section of nodal tissue that delays cardiac impulses from the sinoatrial node to allow the atria to contract and empty their contents and also relays cardiac impulses to the atrioventricular bundle. In order to maintain AV node function, during annuloplasty surgery, a surgeon generally attempts to avoid suturing in or near the AV node. Annuloplasty bands, or C-rings, are, therefore, good choices for use in repair of the tricuspid valve. The annuloplasty bands include a break or opening that may be generally positioned in the area including the AV node in order to avoid the need for suturing in that area. However, since the AV node is not visible to the surgeon, there is the possibility that while securing the endpoints of the annuloplasty band, sutures may be placed in tissue including the AV node.

The AV node is situated in the lower atrial septum at the apex of a triangle known as the Triangle of Koch (TOK), which is an area of heart tissue framed or bounded by certain anatomical landmarks in the heart. Two sides of the TOK are formed by the tendon of Todaro and the septal aspect of the tricuspid annulus. The base is marked at one end by the coronary sinus orifice and the other end by the septal annulus. The region known as the TOK has been the focus of research relating to the cure of supraventricular arrhythmias that arise near the AV node. Additionally, surgical and catheter ablation techniques have made use of the TOK as an anatomic landmark for ablation.

Despite multiple annuloplasty methods and devices currently on the market, there is a continued desire to improve such methods and devices. Particularly, there is a desire to have devices and methods that better accommodate the anatomy of the heart and the shape of the heart throughout the cardiac cycle, and thereby improve results associated with valve repair surgery.

SUMMARY OF THE INVENTION

Annuloplasty devices for the tricuspid valve in the heart and related methods were described in Applicants' co-pending United States Patent Application, having Ser. No. 12/011,482, and filed Jan. 25, 2008, the entirety of which is incorporated herein by reference. One advantage of the annuloplasty devices is that the healthy, native shape of the tricuspid valve may be, which thereby may improve function of the heart valve into which the annuloplasty device is implanted. This close match of normal anatomical shape could also increase durability of the repair by reducing stress on the leaflets. Another advantage is that the annuloplasty device can reduce stress on other parts of the heart, such as the aortic valve for example, and thereby may improve the function of the heart into which it is implanted. An additional advantage is that the annuloplasty device can allow for a greater degree of plication of certain regions of the annulus to improve the function of the tricuspid valve. In particular, the annuloplasty device may reduce the size of the posterior aspect of the annulus, which may thereby improve the function of the tricuspid valve. Yet another advantage is that desired placement of the endpoints of the annuloplasty device can be determined in order to avoid the AV node, such that electrical conductivity through the heart is not affected by the device or sutures used to secure the device in place.

A further advantage of some of the embodiments of the present invention is that when free ends of the annuloplasty device are either flexible or otherwise configured to curve away from the annulus, when the device is implanted, force is distributed away from the endpoints of the device. The annuloplasty devices including flexible ends beneficially allow for a gradual transition between a stiffening element portion of the device and the surrounding tissue of the heart. Also, an advantage of a system including annuloplasty devices of the present invention is that a surgeon may be given more than one choice of an annuloplasty device for a given size of valve annulus. The choice may include, for example, devices having different amounts of compression of the valve, and more specifically compression or reduction of the area of the posterior aspect of the valve annulus. Yet another advantage of a system of the present invention is that sizers may be included that accurately measure the size of a tricuspid valve annulus, which will result in a proper size of annuloplasty device being chosen and implanted.

One aspect of the invention is an annuloplasty device for implantation adjacent an annulus of a tricuspid valve, the annulus comprising anterior, posterior and septal aspects adjacent anterior, posterior and septal leaflets, respectively, of the tricuspid valve, the device comprising: a ring body comprising: an anterior portion, a posterior portion and a septal portion shaped to conform to, and for implantation adjacent, the anterior, posterior and septal aspects of the annulus, respectively; and first and second end portions that are more flexible than a remainder of the ring body to provide a gradual transition from the remainder of the ring body to tissue of the tricuspid valve annulus; wherein the ring body is curvilinear, with substantially no flat portions, and forming a shape. The ring body may be configured such that when the device is implanted, the first end portion will be located near a junction of the septal and anterior aspects of the annulus and the second end portion will be located near the septal aspect of the annulus. The ring body may further comprise: a sheath; and, a stiffening element disposed within the sheath. First and second end portions of the ring body may comprise a flexible material. The stiffening element may comprise a diameter that is reduced towards first and second ends of the stiffening element such that the stiffening element is more flexible towards the first and second ends. The anterior portion may comprise a curve extending in a superior direction, the posterior portion may comprise a curve extending in the superior direction, and the anterior portion curve may extend farther in the superior direction than the posterior portion curve. The ring body may mimic the shape of a native tricuspid valve annulus. The curvilinear shape may include varying slope between four slope minima. The ring body may follow a path from first end portion to second end portion that contains at least two maximum and two minimum positions along the path. Upon implantation, the end portions of the ring body may avoid the AV node of the heart, or the Triangle of Koch of the heart.

A second aspect of the invention is an annuloplasty device for implantation adjacent an annulus of a tricuspid valve, the annulus comprising anterior, posterior and septal aspects adjacent anterior, posterior and septal leaflets, respectively, of the tricuspid valve, the device comprising: a ring body comprising: an anterior portion, a posterior portion and a septal portion shaped to conform to, and for implantation adjacent, the anterior, posterior and septal aspects of the annulus, respectively; and first and second end portions; wherein the ring body is curvilinear, with substantially no flat portions, forming a shape, and the ends are configured such that when the device is implanted, the first end will be located near a junction of the septal and anterior aspects of the annulus and the second end will be located near the septal aspect of the annulus, and the anterior portion comprises a curve extending in a superior direction that includes a peak and the peak will be located within about 20 degrees from the junction of the septal aspect and the anterior aspect of the annulus and located adjacent the anterior aspect of the annulus when implanted. The peak of the anterior portion may be located about 10 to about 20 degrees from the junction of the septal and the anterior aspects of the annulus and located adjacent the anterior aspect of the annulus when implanted. The peak of the anterior portion may be located adjacent the junction of the septal aspect and the anterior aspect of the annulus when implanted. The posterior portion may comprise a curve extending in the superior direction, the anterior portion curve extending farther in the superior direction than the posterior portion curve. The posterior portion may comprise a curve extending in the superior direction, the anterior portion curve extending farther in the superior direction than the posterior portion curve.

A third aspect of the invention is a kit comprising a plurality of annuloplasty devices for implantation adjacent an annulus of a tricuspid valve, the annulus comprising anterior, posterior and septal aspects adjacent anterior, posterior and septal leaflets, respectively, of the tricuspid valve, the plurality of annuloplasty devices each comprising an anterior portion, a posterior portion and a septal portion shaped to conform to, and for implantation adjacent, the anterior, posterior and septal aspects of the annulus, respectively, wherein the plurality of annuloplasty devices are of a given size that correlates to a size of annulus and each comprise a different amount of reduction in the septal-lateral direction to improve septal leaflet coaptation to the posterior and anterior leaflets. The amount of reduction in the septal-lateral aspect may be greater than about 25% and up to about 35%. The plurality of annuloplasty devices may include devices of additional sizes and different amounts of reduction in the septal-lateral aspect.

A fourth aspect of the invention is a sizer device for sizing a tricuspid valve annulus, the annulus comprising anterior, posterior and septal aspects adjacent anterior, posterior and septal leaflets, respectively, of the tricuspid valve, the sizer device comprising: a sizing plate; wherein the sizing plate includes markings that correspond to a junction of the anterior and septal aspects and a junction of the posterior and septal aspects. The shape of the sizing device may mimic the shape of a native tricuspid valve. The sizing plate may comprise an anterior portion, a posterior portion and a septal portion shaped to conform to, and for placement adjacent, the anterior, posterior and septal aspects of the annulus, respectively, in order to size the annulus, and wherein the anterior portion of the sizing plate includes a curve extending in a superior direction that includes a peak and the peak will be located near the junction of the septal aspect and the anterior aspect of the annulus when placed adjacent the annulus. The sizing plate may comprise an anterior portion, a posterior portion and a septal portion shaped to conform to, and for placement adjacent, the anterior, posterior and septal aspects of the annulus, respectively, in order to size the annulus, and wherein the anterior portion of the sizing plate includes a curve extending in a superior direction that includes a peak and the peak will be located about 10 to about 20 degrees from the junction of the septal and the anterior aspects when the sizing plate is placed adjacent the annulus.

It is also contemplated by the present invention that the features of the embodiments described above or elsewhere herein or in the applications incorporated herein by reference may be combined.

BRIEF DESCRIPTION OF THE DRAWINGS

The present invention will be further explained with reference to the appended Figures, wherein like structure is referred to by like numerals throughout the several views, and wherein:

FIG. 20 is a schematic view of another stiffening element of the device that has been opened and laid out providing a 2D view of the circumferential side view of the stiffening element, showing slope minima.

DETAILED DESCRIPTION OF PREFERRED EMBODIMENTS

An annuloplasty device in accordance with the present invention is a non-planar or 3D annuloplasty device. Studies have shown that a functioning tricuspid valve annulus is non-planar, and thus the present invention is particularly suited for repair of the tricuspid valve. Preferably, the annuloplasty device of the present invention mimics either one or both of the 2D and 3D shapes of a healthy, native tricuspid valve annulus, and preferably mimics the shape of a healthy, native valve annulus while in a portion of the cardiac cycle. Most preferably, the annuloplasty device mimics the shape of the healthy, native tricuspid valve annulus while the heart is in systole. The present invention also includes methods of determining the shape of such an annuloplasty device.

The annuloplasty device of the present invention preferably terminates in free ends that when implanted in a tricuspid valve annulus avoid conductive tissue, such as the AV node. An opening or gap in the annuloplasty device between free ends is preferably positioned adjacent the AV node to avoid the need for suturing in that area of the heart. Such an opening or gap may also facilitate appropriate surgical attachment of the device to the annulus when a catheter and/or pacing lead has been placed through the tricuspid valve prior to the surgical procedure. The present invention also includes methods of determining the preferred location of such free ends of the annuloplasty device.

The embodiments of the present invention as shown in the accompanying figures and described herein are particularly designed for or relate to the tricuspid valve. However, the present invention is not limited for application to the tricuspid valve, and it is contemplated that variations of the embodiments may apply to other valves.

Figure 1:
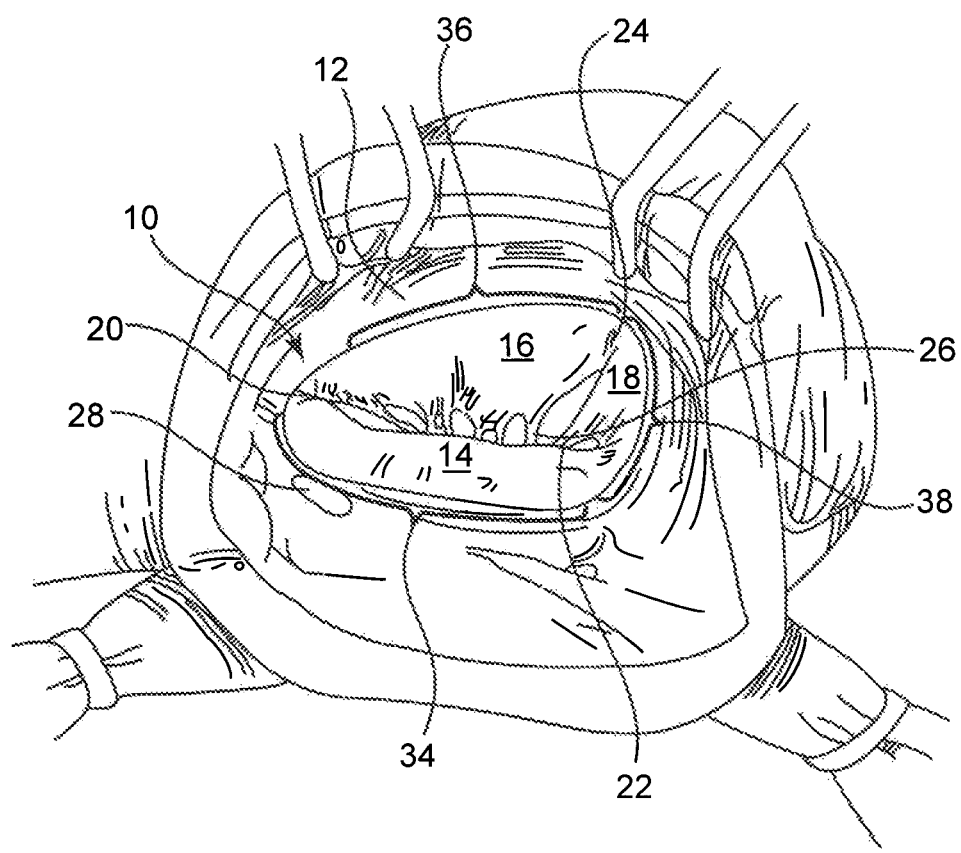
FIG. 1 is a plan view of a tricuspid valve and surrounding anatomy.
Figure 2:
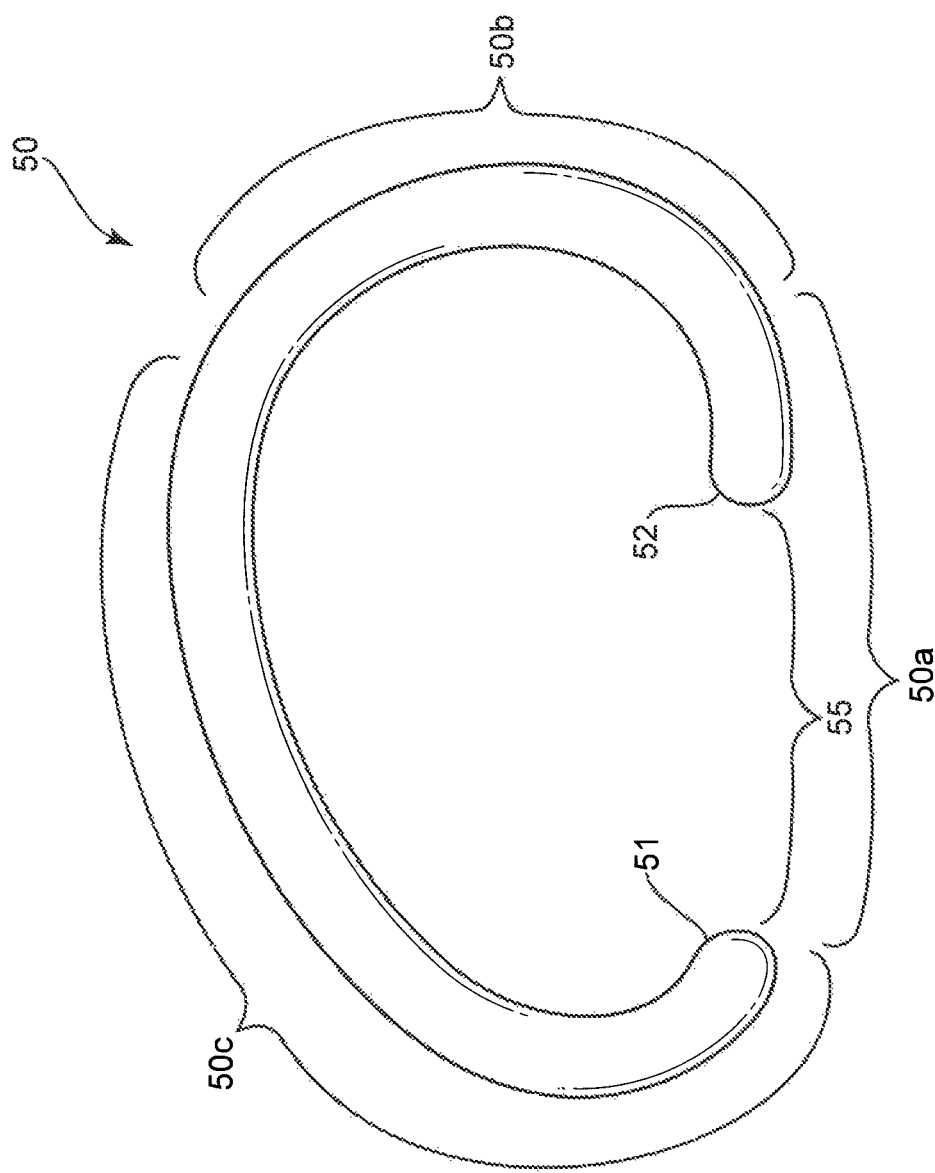
FIG. 2 is a top view of an exemplary annuloplasty band.
Figure 3:
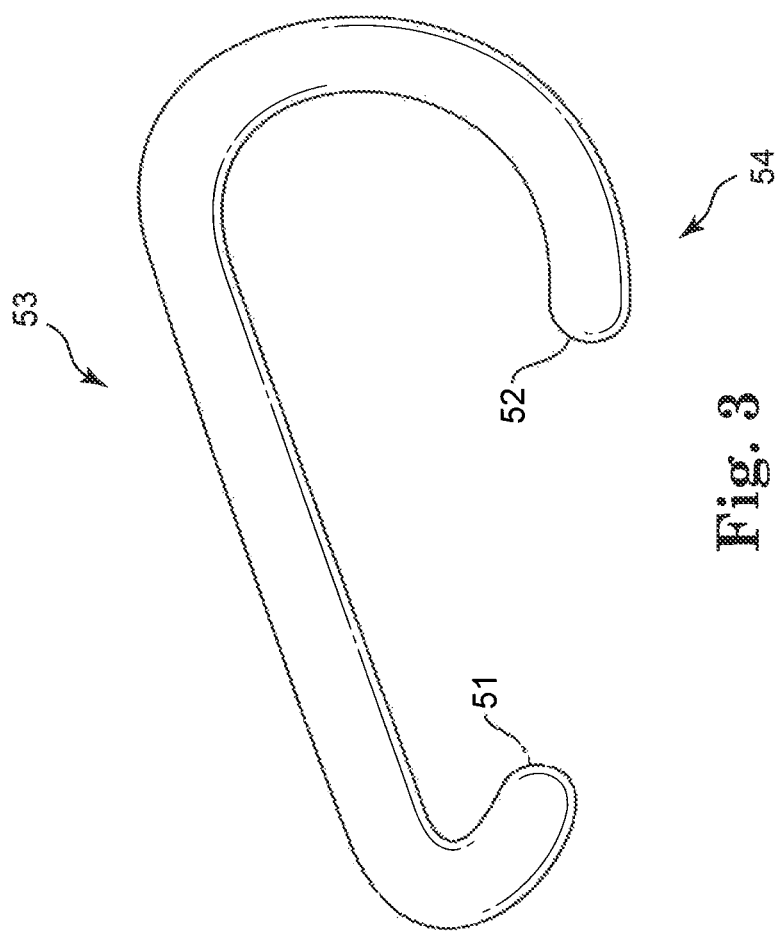
FIG. 3 is an isometric view of the exemplary annuloplasty band of FIG. 2.

With reference to the accompanying figures, wherein like components are labeled with like numerals throughout the several figures, and, initially, to FIGS. 2-6, one embodiment of the first aspect of the present invention is illustrated. FIG. 2 illustrates a top plan view of an annuloplasty band 50. Annuloplasty band 50 is generally arcuate (C-shaped), from a top view, as shown in FIG. 2. Annuloplasty band 50 includes a septal portion 50a adapted to generally be implanted on the septal aspect of a tricuspid valve, a posterior portion 50b adapted to generally be implanted on the posterior aspect of the tricuspid valve, and an anterior portion 50c adapted to generally be implanted on the anterior aspect of the tricuspid valve. The boundaries of the septal, posterior and anterior portions 50a, 50b, 50c of the band 50 are not definite, however, since the drawing may not be to scale and because the anatomy of individual patients may be different (e.g., the lengths of the aspects of different patients' valve annuli may be different).

As discussed earlier, the terms anterior and posterior, with regard to the leaflets of the valve, are also referred to as anterosuperior and inferior, respectively. Both terms may be used interchangeably. However, the present application will use the terms anterior and posterior.

When implanted, a first free end 51 and a second free end 52 of the annuloplasty band 50 may preferably be sutured to the septal aspect of the annulus. An opening or gap 55 is preferably present between the two free ends 51, 52. Such an opening or gap preferably may cooperate with the region of the annulus between the anteroseptal and posteroseptal commissures (i.e., the septal portion of the annulus). An opening or gap length can range between 0 mm (with the free ends touching) and the full distance between the anteroseptal and posteroseptal commissures. Preferably, the first end 51 extends past the anteroseptal commissure along the septal aspect of the annulus, when implanted, so that at least one suture can be made beyond the anteroseptal commissure along the septal aspect of the annulus for stability of the septal aspect.

FIGS. 3-6 illustrate an isometric view, a side view, a view from the anterior portion end and a view from the posterior portion end, respectively, of the annuloplasty band 50 of FIG. 2. FIGS. 3-6 show that the annuloplasty band 50 preferably has a 3D shape that has a sloped profile in the directions superior and inferior to the tricuspid valve annulus. The term "superior" as used herein refers to above the tricuspid valve annulus. The term "superior direction" as used herein refers to the direction extending above the tricuspid valve annulus, meaning generally towards the head while the tricuspid valve annulus is in place and oriented in the body. The term "inferior" as used herein refers to below the tricuspid valve annulus. The term "inferior direction" as used herein refers to the direction extending below the tricuspid valve annulus, meaning generally towards the feet while the tricuspid valve annulus is in place and oriented in the body. The 3D shape shown is one exemplary shape/configuration, however, other 3D shapes are also contemplated by the present invention, which may mimic the native, healthy shape of the tricuspid valve annulus and/or that may improve function of the tricuspid valve.

Figure 4:
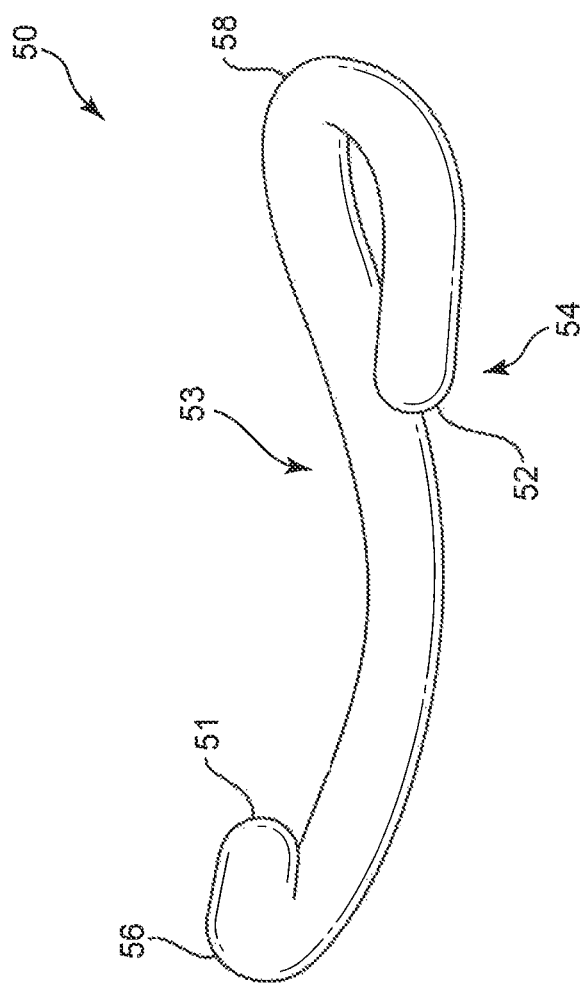
FIG. 4 is a side view of the exemplary annuloplasty band of FIG. 2.
Figure 5:
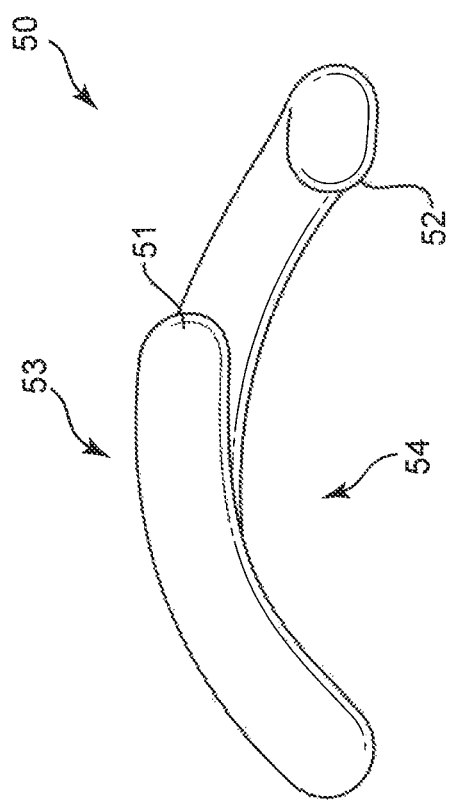
FIG. 5 is a view from anterior portion end of the exemplary annuloplasty band of FIG. 2.
Figure 6:
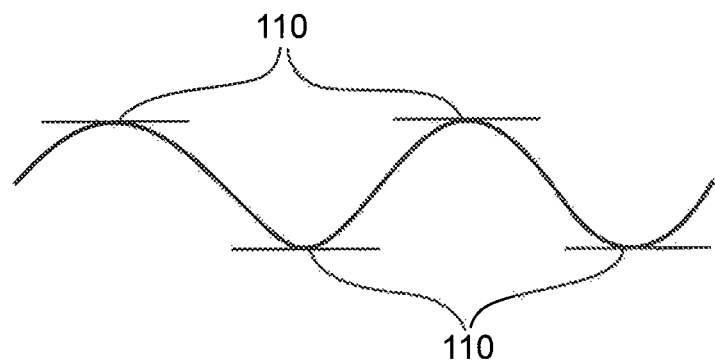
FIG. 6 is a schematic view of a stiffening element of the device that has been opened and laid out providing a 2D view of the circumferential side view of the stiffening element, showing slope minima.

First 53 and second 54 sides of the annuloplasty band 50 are indicated in FIGS. 4-6. If the annuloplasty band 50 was implanted in a valve annulus, blood flow would generally flow through from first side 53 to second side 54. In other words, if implanted, the first side 53 of the annuloplasty band 50 is preferably adjacent the atrial side of the valve and the second side 54 is preferably adjacent the ventricular side of the valve. Blood flow should be from superior to inferior or in the inferior direction as defined above.

The embodiment shown in FIGS. 2-6 includes an opening or gap 55 of a certain size. Different embodiments of the annuloplasty device of the present invention may have different sized openings or gaps between two free ends of the annuloplasty device. The purpose of a smaller opening may be to provide additional support for anchoring the device to the valve annulus. The benefit of having a larger opening, however, may be that fewer sutures are necessary in the septal portion of annulus to attach the device, which reduces possible effects caused by suture placement in and around the AV node. Moreover, as the septal leaflet has a lesser tendency to dilate, there is less of a need for the septal annuloplasty band portion to extend farther along the septal aspect of the annulus.

The preferred shape of the annuloplasty device of the present invention is substantially similar to the shape of a healthy, native tricuspid valve annulus. In general, the preferred shape is curvilinear and continuously varying or curving, and includes substantially no flat portions, from first free end to second free end. "Flat" means non-curved in any of three dimensions. The anterior, posterior and septal portions of the device together form the shape of the ring body. The anterior and posterior portions preferably comprise curves or bowing extending in a superior direction. The anterior portion curve or bow extends farther in the superior direction than does the posterior portion curve. The shape of the ring body preferably emulates or mimics the shape of a healthy, native tricuspid valve annulus. Most preferably, the shape is determined in systole. The band is preferably configured such that the first and second free ends 51, 52, when sutured to the annulus, are located at or near the anteroseptal commissure and along the septal aspect of the annulus, respectively.

With reference to FIGS. 2-6, one example of the preferred curvilinear and continuously varying or curving shape of the device as described above is shown. The band 50 comprises a curvilinear shape with a curve 56 (FIG. 4) in the anterior portion extending in the superior direction and a curve 58 (FIG. 4) in the posterior portion also extending in the superior direction. The anterior portion curve 56 extends farther in the superior direction than does the posterior portion curve 58. Preferably, the curve 56 in the anterior portion may be sutured at or near the aortic valve when the device is implanted in an annulus. The shape in FIGS. 2-6 is believed to emulate the shape of a healthy, native tricuspid valve annulus. However, other possible shapes are also contemplated.

In the case of an annuloplasty device of the present invention that includes two free ends, their preferred location is as follows: the first free end being configured and sized for a select tricuspid valve size to be located near and slightly beyond the junction of the anterior and septal portions; and, the second free end being located along the septal portion. The first and second free ends, when the device is implanted in an annulus, will preferably correspond to a location near the anteroseptal commissure (junction of anterior and septal aspects) and along the septal portion, respectively. Another preferred location for the two free ends is that both free ends will be located in the septal portion of the device and, when implanted, correspond to the septal aspect of the annulus. Preferably the two free ends are to be located to avoid suturing of the ends near the area of the heart that includes the AV node, which could negatively affect conductivity relating to the AV node.

With reference to FIG. 2, the first free end 51 is generally shown at or near the junction of the anterior portion 50c and the septal portion 50a or near the anteroseptal commissure when implanted. The second free end 52 is generally shown in the septal portion 50a. The figure is not, however, to scale, and represents one location for the two free ends 51, 52. Other locations for the free ends of an annuloplasty band in accordance with the present invention are, however, also contemplated by the present invention.

The annuloplasty device of the present invention may include various 3D shapes. As described above, a preferred 3D shape is curvilinear and continuously curving around its perimeter with substantially no flat portions. The preferred shape includes a curve in the anterior portion that extends in the superior direction and a curve in the posterior portion that extends in the superior direction, with the anterior portion curve extending farther in the superior direction than the posterior portion curve. The curve in the anterior portion is preferably configured to be located near the aortic valve when the device is implanted around a tricuspid valve annulus.

In another embodiment, however, the 3D shape of a device, for example, may be described as a curvilinear shape with a generally varying slope between four minima (e.g., slope minima). The 3D, curvilinear slope is defined in the directions superior and inferior with respect to the tricuspid annulus. FIG. 6 schematically and generally illustrates this concept by showing a stiffening element of the present inventive device that has been opened and laid out, providing a 2D view of the circumferential (or perimeter) side view. The "slope minima" and "minima" and "minimum slopes" referred to with regard to FIG. 6 are indicated by 110. The location of the minimum slopes 110 can be varied around the perimeter of the ring corresponding to specific anatomical locations in order to preferably mimic a natural anatomic shape, which may provide improved valve function and reduce leaflet stress. A period in the curvilinear shape between the slope minima 110 can also be adjusted by increasing or decreasing the rate of slope change between the four slope minima 110, which may allow for both variable amplitude and spacing between slope minima 110. The spacing between neighboring slope minima 110 preferably is at least one eighth of the perimeter of the device and is preferably no greater than half the perimeter of the device, which may control the amplitude and slope between neighboring slope minima 110.

Figure 7:
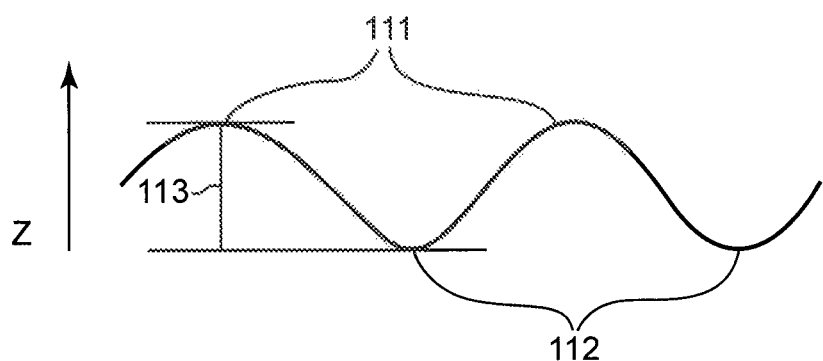
FIG. 7 is a schematic view of a stiffening element of the device that has been opened and laid out providing a 2D view of the circumferential side view of the stiffening element, showing maximum and minimum positions and range between them.

In another embodiment, the 3D shape of the device may be described as a curvilinear shape that follows a path around the perimeter of the ring that contains at least two maximum and two minimum positions along the path. FIG. 7 schematically illustrates this embodiment by showing a side view of a stiffening element of the present inventive device that has been opened and laid out providing a 2D view of the circumferential side view of the stiffening element. The maximum positions 111 and minimum positions 112 can occur at desired positions along the perimeter of the device and correspond to desired positions along the annulus in order to preferably mimic the natural anatomical shape of the annulus, which may provide improved valve function and reduce leaflet stress. A preferred range 113 between any maximum 111 and minimum 112, as shown in FIG. 7, may be no less than 10% of the linear distance 114 between the anteroseptal 115 and posteroseptal 116 commissures, as shown with regard to an annulus 119 in FIG. 8.

Figure 8:
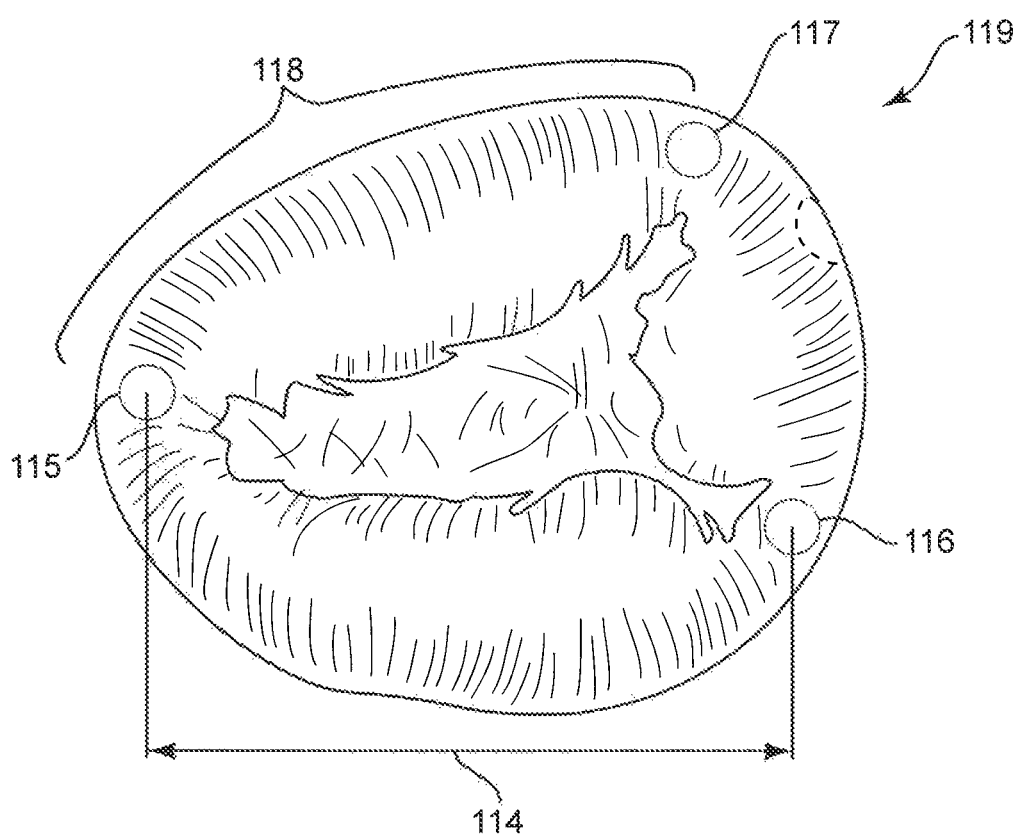
FIG. 8 is a top view of a tricuspid valve annulus, indicating positions of the commissures.

In yet another embodiment, the 3D shape of the device may be described as a curvilinear, and 3D or non-planar ("non-planar" defined in the directions superior or inferior with respect to the tricuspid annulus) shape along a span of the device that mates with an annular region 118 of an annulus 119, as that shown in FIG. 8 with the annular region 118 extending between the anteroseptal 115 and anteroposterior commissures 117. The non-planar shape may preferably span at least 30% of the arc length (i.e., length of the annulus along the perimeter of the annulus) between the anteroseptal 115 and anteroposterior 117 commissures, with a minimum height (extending in the directions superior or inferior with respect to the tricuspid annulus) above or below the annulus 119 of at least 5% of the linear distance 114 between the anteroseptal 115 and posteroseptal 116 commissures.

The annuloplasty device of the present invention comprises a ring body that comprises a sheath or covering and a stiffening element within the sheath or covering. The annuloplasty device body preferably further comprise an opening or gap between two free ends of the covered stiffening element. Details of the components are provided below.

The stiffening element portion of the annuloplasty device of the present invention is preferably designed to be covered and implanted in a tricuspid valve annulus. In general, the stiffening element imparts a shape to the annuloplasty device, and is adapted to remodel, preferably, the tricuspid valve annulus. The stiffening element may comprise a metal, ceramic, polymer or a composite, for examples. Some desirable properties of suitable materials for use in the stiffening element include, but are not limited to, biocompatibility, biostability, and corrosion- and fatigue-resistance. In some embodiments, the stiffening element is made of a material that imparts rigidity to the stiffening element, which in turn imparts rigidity to the annuloplasty band. If the stiffening element comprises a metal wire, the wire can be formed of any medically-acceptable, implantable, biocompatible metal, such as cobalt-nickel alloy (MP35N™), cobalt-chromium alloy (Elgiloy™, Haynes 25™), titanium, stainless steel, shape memory materials such as nickel-titanium alloy (Nitinol™), or other similar inert biocompatible metal.

The stiffening element may generally have a circular cross-section. However, cross-sections of other shapes are also contemplated by the present invention (e.g., square, rectangular, elliptical, triangular, or the like). Different cross-sectional shapes can be used to impart varying degrees of bending or torsional stiffness depending on the bending/twisting plane with respect to the section modulus. Also, the cross-sectional shape may be varied around the perimeter of the stiffening element, which may vary the stiffness around the perimeter.

Preferably, the stiffening element may be covered or overmolded with a biocompatible, biostable, implantable medical grade elastomeric protective coating, such as an elastomeric thermoplastic polymer (e.g., polyurethane) or a silicone (e.g., liquid silicone rubber) to provide a consistent profile and to create desirable needle penetration properties for the surgeon. Also, coating can impart radiopaque and echogenic in vivo visualization, for example. Alternatively, the protective coating may be tubing within which the stiffening element is disposed, the tubing consisting of biocompatible, biostable, implantable medical grade elastomeric material, such as elastomeric thermoplastic polymer (e.g., polyurethane) or silicone. In yet other embodiments, the protective coating may be eliminated.

The stiffening element, with or without the protective coating, is preferably covered with a sheath or covering. The covering or sheath may comprise a knitted polymeric fabric (e.g., polyethylene terephthalate or Dacron™), although woven, non-woven materials (e.g., spun-bond, melt-blown, staple fiber matrix, etc.), braided fabrics, or metallic braids (e.g. titanium, Nitinol, and stainless steel wires) are also contemplated, as well as sheaths formed of harvested biological tissue (e.g., pericardial tissue). The covering or sheath may optionally be provided with any of various biocompatible coatings. The preferred purpose of the covering or sheath is to provide a site for attachment of the device to the annulus using invasive or minimally invasive surgical techniques as well as to allow for in-growth of the device with the native valve tissue. A plurality of knotted sutures is typically used to secure the annuloplasty device to the tricuspid annulus, although other fasteners such as staples, fibrin glue, or the like may be used.

Figure 15:
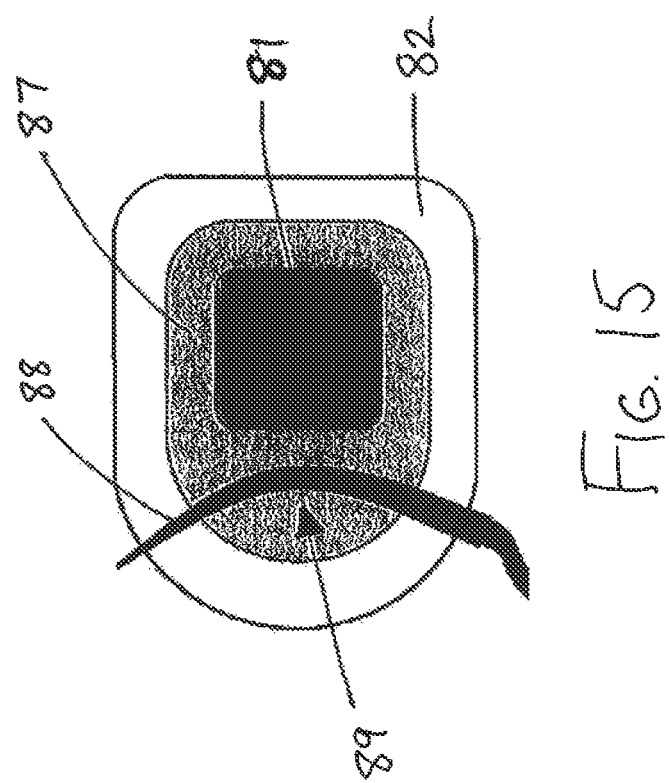
FIG. 15 is a cross-sectional view of an exemplary annuloplasty band including the stiffening element, a coating layer, and a sheath.

A preferred cross-sectional shape for a stiffening element is shown in FIG. 15, wherein a stiffening element 81 has a generally square cross-section. An elastomeric coating 87 and a sheath 83 are also illustrated in cross-section, respectively, as overlaying the stiffening element 81. The coating 87 can be provided as overmolded or coated onto the stiffening element 81, such as by any conventional overmolding or coating technique. Or, the coating 87 can be provided as a tubing or hose of elastomeric material with an open central lumen of a size and shape to receive the stiffening element 81 (in the preferred case, as a square lumen). An advantageous feature of the coating 87 that is illustrated in FIG. 15 is the provision of an enlarged portion 89 that is provide on one side of the stiffening element 81. As shown, the enlarged portion is provided to a side surface that is along an outer circumference of the annuloplasty band or ring body to facilitate easier suturing of the annuloplasty band to the tissue of a tricuspid valve annulus. A suturing needle 88 is shown as passing through the enlarged portion 89 of the coating 87 as part of a suturing step. The size and shape of this enlarged portion 89 can be varied for the purpose of facilitating any specific suturing technique, and it is contemplated that other surfaces of the stiffening element can be otherwise or additionally provided with a similar or different enlarged portion for similar purposes, as may be needed to improve suturing to tissue at specific annulus locations. In this regard, it is further contemplated that the coating 87 can vary along its length for this or similar purposes.

The stiffening element may also be radiopaque, echogenic, MRI-compatible and/or otherwise imaging enhanced so that it may readily be visualized after implantation using various existing techniques or any future developed techniques, including x-ray, MRI, echogram, etc. By "radiopaque," it is meant that the material or element prevents the passage of radiation. "Radiation" is meant to include electromagnetic energy, light, etc. By "echogenic," it is meant that it reflects sound waves. By "MRI-compatible" it is meant that the material or element is both MRI safe and capable of being excited by MRI.

The annuloplasty device of the present invention may have any amount of flexibility. Preferably, the device has a sufficient elasticity that allows the band to return to an original shape after physiologic forces are applied and removed to the device and the device is in a free state. For example, the device may be rigid or semi-rigid. The rigidity of the device may be varied depending upon the material comprising the device and/or the construction of the device. For example, the rigidity of the device can also be controlled by controlling the material and shape/size of the cross section of the stiffening element.

In some embodiments of the present invention, in particular any embodiments having a stiffening element comprising a semi-rigid material and two free ends, the stiffening element may have eyelets (not shown) at one or both of its two free ends, which may be used to suture the ends and anchor them to fibrous tissue of the annulus (e.g., the septum). The eyelets may be formed by the stiffening element being bent back onto itself at one or both of the first and second free ends. Alternatively, the eyelets may be integrally molded with the rest of the stiffening element, or can be subsequently assembled to the stiffening element. As used herein, "eyelet" means an opening with a substantially closed perimeter, but does not require a specific shape (e.g., an eyelet can be round, square, rectangular, trapezoidal, hexagonal, tear-drop, oval, elliptical, or any other suitable shape), although shapes with lower stress concentrations are preferred. The eyelets are preferably adapted to receive at least one suture to secure the annuloplasty device to a valve annulus or a heart valve, such as the tricuspid valve.

In some embodiments, one or both of the free ends of the ring body would include a more flexible or compliant segment or portion. Alternatively, end portions of the ring body may have reduced stiffness from the remainder. One purpose of the more flexible or less stiff segment would be to allow for a more gradual compliance of the device with surrounding tissue at one or both of the ends of the ring body. The flexible or less stiff segments allow for a gradual transition from the stiffening element of the device to the surrounding tissue. The more flexible or less stiff ends also allow force to be distributed away from the endpoints of the stiffening element.

Figure 13:
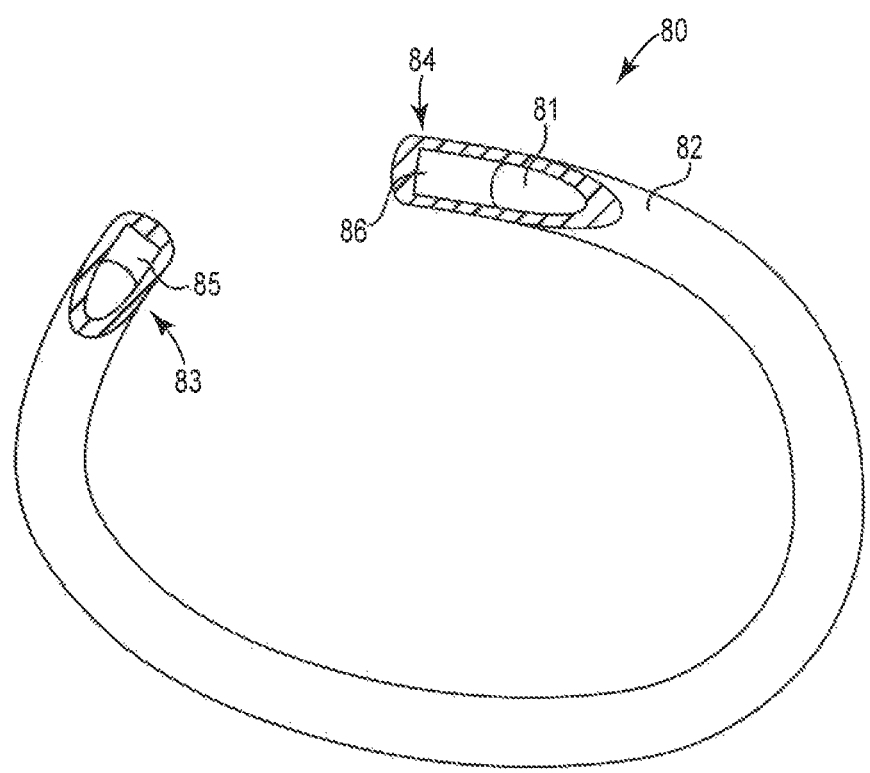
FIG. 13 is a top and partial-cut-away view of an exemplary annuloplasty band.

The flexible segments may be formed by providing an amount of flexible or complaint material to one of both of the free ends of the stiffening element, for example. Such flexible material can be attached to an end of the stiffening element or positioned there and otherwise restrained in place. In the case of the provision of an elastomeric coating 87, as described above, to the stiffening element 81, the elastomeric coating can be extended to provide the flexible material as extending beyond the end or ends of the stiffening element. FIG. 13 shows a tricuspid valve annuloplasty device 80 in a top, partial cut-away view. The band 80 comprises the stiffening element 81 that is surrounded by sheath or covering 82. The sheath 82 is partially cut away at end sections of the device 80 in the figure, allowing inside of the ends 83, 84 of the device to be seen. One or both of the ends of the stiffening element 81 can have extension segments of a more flexible or complaint material, such as shown at both ends as elements 85 and 86, than the remainder of the stiffening element. These extension segments 85, 86, can be made separately from the stiffening element 81 and attached thereto. If separately made, such segment can be connected with the free ends of the stiffening element, such as by an adhesive, welding, or the like, may be just positioned there and held in place by constraint of the sheath 82, or may be provided as an extension of a coating that is applied to cover the stiffening element 81. Alternatively, in an integrated design, a flexible extension could be provided as an extension of the stiffening element that is effectively decreased in diameter or changed in its cross-sectional shape toward the free ends 83, 84, of the device 80, which would make the extension or extensions of the stiffening element 81 more compliant or more flexible in those areas. It is contemplated that variations of flexibility or the stiffness and/or shape can vary as well along these more compliant segments 85 and/or 86. Thus, a controlled force distribution for one or both ends of the stiffening element of the ring body can be designed into the ring body. Then, when the ring body is sutured to the tricuspid valve annulus, for example, the force at one or both ends as is generated to the annulus at the ring body ends as a result of suturing can be controllably distributed to the adjacent tissue including the portion of the annulus that is within the gap that is provided between the ends of the ring body including the AV node. Another advantage of such force distribution at the ring body ends is a to reduce the likelihood of late dehiscence near the ends of the ring body within the annulus tissue as a result of suturing the ring body to the annulus. That is, forces that might tend to split sutured tissue are spread out or distributed to adjacent tissue to reduce the likelihood of such tissue dehiscence.

An exemplary material that may be used for the flexible or compliant extension segments 85, 86 is an elastomeric material, such as silicone. Other materials and combinations of materials are also contemplated by the invention, however, and are not limited to those described herein.

In a preferred embodiment, the flexible or compliant extension segments are about 1-10 mm in length, preferably extending over at least the last 3-5 mm of the device, however other lengths are also contemplated as effective to provide a desired controlled force distribution at one or both of the ends. Ends can have similar or different lengths of flexible extension as determined for effective controlled force distribution, as desired. The lengths of the segments function to provide a desired amount of gradual transition between the stiffening element and the ends of the device. For effectiveness, it is preferred that any such flexible extension have a length that is at least greater than the cross-sectional dimension or diameter of the stiffening element.

The flexible extension segments may be shaped in order to be useful for a given device and purpose. For example, the cross-section of the flexible extension segment may be circular, but other shapes are also contemplated, which shape changes can be utilized as part of a controlled force distribution at one or more of the ring body ends.

When implanted, one end of the device may be placed at or near the antero-septal commissure in the valve annulus and the other end may be placed at or near the septal aspect of the annulus (most preferably, at or near the middle of the septal aspect). With a device that includes one or both flexible extension segments, then the ends of the stiffening element may be located at the same position as described above, with the flexible extension segments extending further along the circumference of the valve annulus for controlled force distribution beyond the ends of the stiffening element. The provision of such a flexible extension is of particular benefit when provided at the end of the stiffening element that is to be positioned along the septal aspect of the annulus. It is along the septal aspect of the tricuspid annulus that dehiscence is more likely to occur after implantation of the ring body. The result of a controlled force distribution at this end of the ring body along the septal aspect is a reduction of the likelihood of such dehiscence. Alternatively, however, the ends of the flexible extension segments may be located at or near the positions described above. The invention contemplates, however, that various combinations of end point locations may be used.

In some embodiments, construction of the annuloplasty device preferably provides a low profile attribute. More particularly, the cross-sectional diameter or width would preferably range from about 0.03 to about 0.20 inches, with the stiffening element portion having a cross-sectional diameter or width ranging from about 0.005 to about 0.150 inches. However, other ranges of diameters and widths are also contemplated by the present invention. A purpose of the low profile is to minimize disturbance to blood flow and potential thrombus formation.

Figure 9:
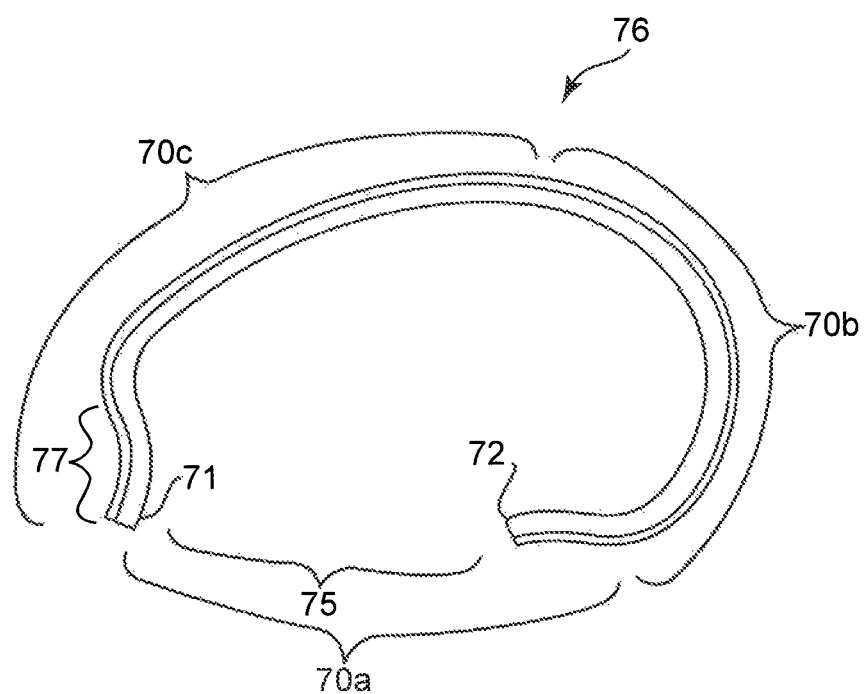
FIG. 9 is a top plan view of an exemplary stiffening element forming one structural component of an exemplary annuloplasty band of the present invention.

A stiffening element portion of another embodiment of the annuloplasty device of the present invention is shown in FIG. 9. The stiffening element 76, seen in a top plan view, has an opening or gap 75 between two free ends 71, 72 of the stiffening element, and an inward curvature 77 in the anterior portion 70c, which corresponds to an anterior aspect of an annulus, and near the first free end 71. The inward curvature 77 curves inward toward the flow or valve orifice in the region that may interface with an anterior aspect of an annulus and that may be located near an aortic valve when a device including the stiffening element 76 is implanted adjacent a tricuspid valve annulus. The inward curvature 77 can allow the aortic valve to open more fully because the stiffening element 76 of the device does not enter or protrude into the area of the aortic valve and avoids the aortic valve. As a result of avoiding the aortic valve, the curvature 77 can minimize distortion of the aorta during a cardiac cycle. This embodiment may be combined with the 3D shapes of the device that are described above.

Figure 10:
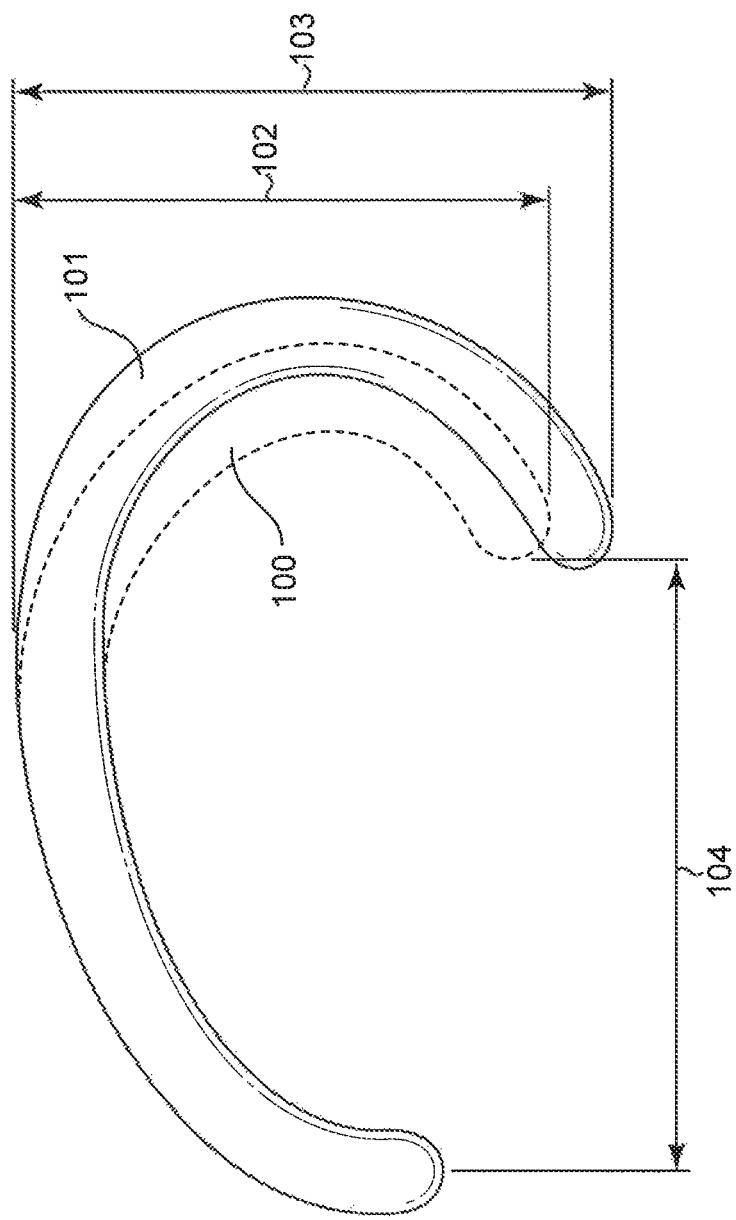
FIG. 10 is a top plan view of an exemplary annuloplasty band shown overlapping an annuloplasty band of the same size but that includes a reduced posterior and anterior portion.

Another optional feature of the present invention allows for overcorrection of valve dilation along the posterior aspect of the tricuspid annulus by reducing the length of the posterior portion of a ring relative to a measured valve size. FIG. 10 illustrates how the length of the posterior annulus portion may be reduced to correct valve dilation. In FIG. 10, two annuloplasty bands 100 (demonstrating this embodiment of the present invention) and 101 (an exemplary prior art band) are laid one on top of the other so that the anterior portions and the free ends near the anterior portions are aligned. The septal-lateral, otherwise known as the septal-anterolateral, distance 102 of the portion of the stiffening element 100 corresponding to the posterior aspect of an annulus is shorter than the length 103 of the portion of stiffening element 101 corresponding to the posterior aspect. The distance 104 between the free ends in both stiffening elements 100, 101, however, for both bands is shown as substantially the same. As can be seen in FIG. 10, the reduction in the length of the posterior portion 102 from posterior length 103, while maintaining the distance between the free ends 104, results in a reduced curvature along the posterior region of the stiffening element 100 from stiffening element 101. Since the size of an annuloplasty device may be dependent upon the distance between the free ends, the result is a stiffening element 100 of generally the same size as stiffening element 101, but with a reduced curvature along the posterior portion. The purpose of this embodiment of the present invention is to ensure sufficient leaflet coaptation without global downsizing of the valve annulus. This embodiment may be combined with the 3D shapes of the device that are described above.

According to preferred aspects of the present invention, an annuloplasty band 100 is designed to have at least about 25% reduction of the septal-lateral dimension over the anatomical measurements of a typical tricuspid valve annulus. Moreover, it is preferable to provide a reduction of between 25% and about 33% for improved effectiveness in coaptation of the valve leaflets. That is to say, that if the illustrated band 101 were to have a curvature in the posterior region thereof, in the plan view as shown in FIG. 10, that includes a septal-lateral dimension indicated by 103 that is based upon a measured septal-lateral dimension of a tricuspid annulus, a preferred band 100 would have at least a 25% reduction of the septal-lateral dimension so as to enhance coaptation between the leaflets. As illustrated, the reduction of curvature of the posterior region of the band 100 reduces the septal-lateral dimension of the band 100 to the dimension 102 (as compared with a measured anatomical septal-lateral dimension) and also reduces a dimension 105 between the end of the band to be implanted near or at the anteroseptal commissure (junction of anterior and septal aspects) and the inside curvature of the posterior region of the band 100. Based upon this combination of reductions in design of the band 100, as compared to measured anatomical dimensions, coaptation of the septal to the anterior leaflets is enhanced as is the coaptation of the posterior leaflet with both the septal and anterior leaflets. Coaptation between all of the tricuspid leaflets is effectively enhanced. With insufficiency of a tricuspid valve annulus, it is often the case that the right ventricle becomes enlarged and increased cinching of the tricuspid annulus, as the effect of a reduction of the septal-lateral dimension, effectively enhances coaptation of the leaflets and valve performance efficiency.

The invention also contemplates a system or kit of annuloplasty devices that provides several different sizes of tricuspid valve annuloplasty devices. Any number of different sizes, but preferably at least six sizes of devices will be included in the system or kit, with preferred sizes including at least 26 mm, 28 mm, 30 mm, 32 mm, 34 mm, and 36 mm. These sizes are based upon a measured anatomical size of certain common tricuspid valve annulus sizes. However, other sizes of devices are also contemplated by the invention.

The invention also contemplates a system or kit of annuloplasty devices of either one size or multiple sizes in which the system or kit includes more than one annuloplasty device of a given anatomical size that have different septal-lateral dimensions or lengths of the posterior portion of the device (i.e., different amounts of compression of the posterior aspect of the annulus). Preferably, devices having reduced lengths of the posterior portion will be provided, although it is contemplated that a different dimensional aspect of a variety of bands all relating to a common anatomical size can be combined in accordance with this aspect of the present invention. The purpose of the reduced length of the posterior portion, as discussed above, is to reduce curvature along the posterior region of the device, which may enhance leaflet coaptation without global downsizing of the valve annulus. The different lengths of posterior portions may result in different levels of coaptation of the leaflets of the valve. In particular, as above, it is preferred that a preferred band in accordance with the present invention include at least a 25% amount of reduction or compression. It is contemplated that such a reduction can be increased to as much as about 33%. Devices having different percentages of compression, or different compression ratios (e.g., 5%-33%), however, may be provided and are contemplated. Therefore, the invention includes a kit of devices that may have one size or multiple sizes, and for each size there are, for example, a plurality (e.g., 2 to 5) different devices available in that size to a physician during surgery that include different levels of compression or reduction of the septal portion (effecting a reduction in the septal aspect of the annulus upon implantation).

The present invention also contemplates a system that includes holders and sizers correlating in shape and size to the annuloplasty device of the present invention, which may differ in size and shape. Such holders assist in implantation of a ring or band in a patient, and such sizers assist in choosing the correct size of device for a given valve or valve annulus of a patient.

Figure 14:
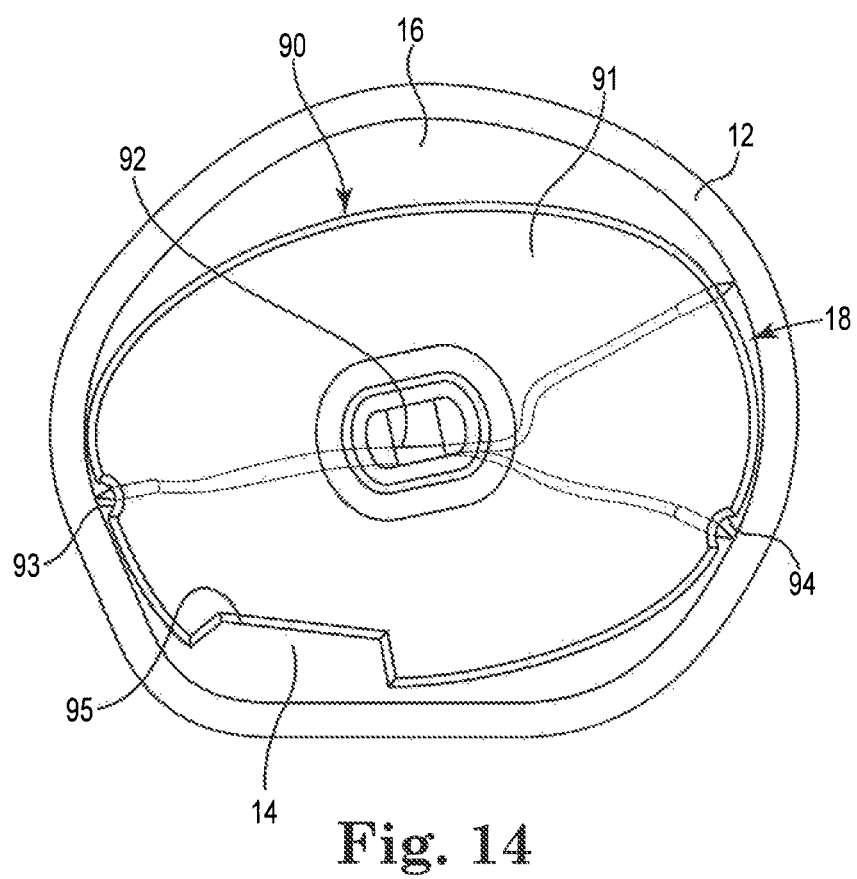
FIG. 14 is a top view of a sizer device located adjacent a tricuspid valve annulus.

Sizers are used to size the tricuspid valve annulus prior to a surgeon choosing a particular device for annuloplasty surgery. Another aspect of the invention is a sizer that accurately measures the anatomical dimensions of a tricuspid valve annulus. Inventive sizer devices in accordance with the present invention measure the septal leaflet, or septal aspect of the annulus, which allows the correct size of annuloplasty device to be chosen to be implanted in the tricuspid valve annulus. A sizer device 90 is shown in FIG. 14 as it is used to size a tricuspid valve annulus 12.

The sizer device 90 comprises a sizing plate portion 91 that is shaped to correspond to annuloplasty devices of the present invention. Thus, the sizing plate portion 91 may include two-dimensional (2-D) shape and/or three-dimensional (3-D) shape corresponding to those described annuloplasty devices. The sizing plate 91 preferably comprises a material that a surgeon can see through in order to see the leaflets of the heart valve (14, 16, and 18 in FIG. 14, with dashed lines indicating where the leaflets coapt together) and ensure proper sizing.

The sizer device 90 also comprises an attachment hub 92 that is generally in or near the center of the sizing plate 91, and allows an elongate member (not shown) to attach to the sizer device 90 and be used to deliver the sizer device 90 within close proximity of the tricuspid valve annulus for sizing of the annulus. The attachment hub 92 preferably allows the sizer device 90 to be removably attached to the elongate member.

The sizing plate 91 preferably includes markings, indentations or cut-out portions 93 and 94 that will correspond to a patient's commissures. In particular, a cut-out 93 is illustrated that corresponds to the anteroseptal commissure and a cut-out 94 is illustrated that corresponds to the posteroseptal commissure. The cut-outs 93, 94, therefore, determine an effective dimension of the septal leaflet of the valve.

The sizing plate 91 also preferably includes a gap 95 that corresponds to an opening or gap in an annuloplasty device between two free ends of the device, as described herein with regard to the inventive annuloplasty devices. As shown, the gap portion 95 corresponds to a gap where a first end of a annuloplasty device extends further past the anteroseptal commissure and along the septal aspect while the second end is to be located also along the septal aspect in a more mid-point thereof.

FIG. 4 shows an annuloplasty device of the present invention with a superior-extending curve 56 in the anterior portion. The peak of the curve may be alternatively be located at various locations along the anterior portion of the device. One embodiment even includes the peak of curve 56 being located at the anteroseptal commissure when the device is implanted. Other embodiments locate the peak of curve 56 between about 10 degrees to about 20 degrees clockwise from the anterospetal commissure, for example. Two preferred embodiments include the peak of the anterior curve at 10 degrees and 20 degrees from the anteroseptal commissure.

A marking of the anteroseptal commissure attachment point is preferably included on the embodiment of the annuloplasty device of the invention. The marking may assist a surgeon in implanting the device, such that the marking is lined up with the anteroseptal commissure during implantation. A marking of the posteroseptal commissure attachment point may also be included on the device.

The devices and sizers of the invention include 2-D and/or 3-D shapes that complement each other. Therefore, the sizers of the invention also preferably include a curve in an anterior portion that corresponds to the curve 56 of the device 50. The sizer 90, with or without the curve, preferably is marked where the sizer is to be lined up with the anterospetal commissure upon implantation (as discussed above). The peak of the anterior curve of the sizer 90 may be located so as to line up with the anteroseptal commissure upon implantation, or alternatively be located between about 10 degrees to about 20 degrees clockwise from the anteroseptal commissure.

The present invention relates to methods of determining the shape and configuration of an annuloplasty device used to repair a tricuspid valve. One method is for determining a shape of an annuloplasty device for tricuspid valve repair, the method comprising the steps of: determining specific anatomical features of a heart; determining the shape of the tricuspid valve annulus in the heart; and using the anatomical features of the heart and shape of the annulus to determine the shape of the annuloplasty device. At least one of the determining steps may be performed using at least one imaging technique on at least one heart. The at least one imaging technique may be selected from the group consisting of: radiographic means, echogenic means, computed tomography, magnetic resonance imaging, other currently existing imaging processes, or any future developed imaging techniques. The method may further comprise the steps of: using the anatomical features of the heart to determine the Triangle of Koch; and locating free ends of the device such that the free ends will not contact the Triangle of Koch when the device is implanted.

Figure 16:
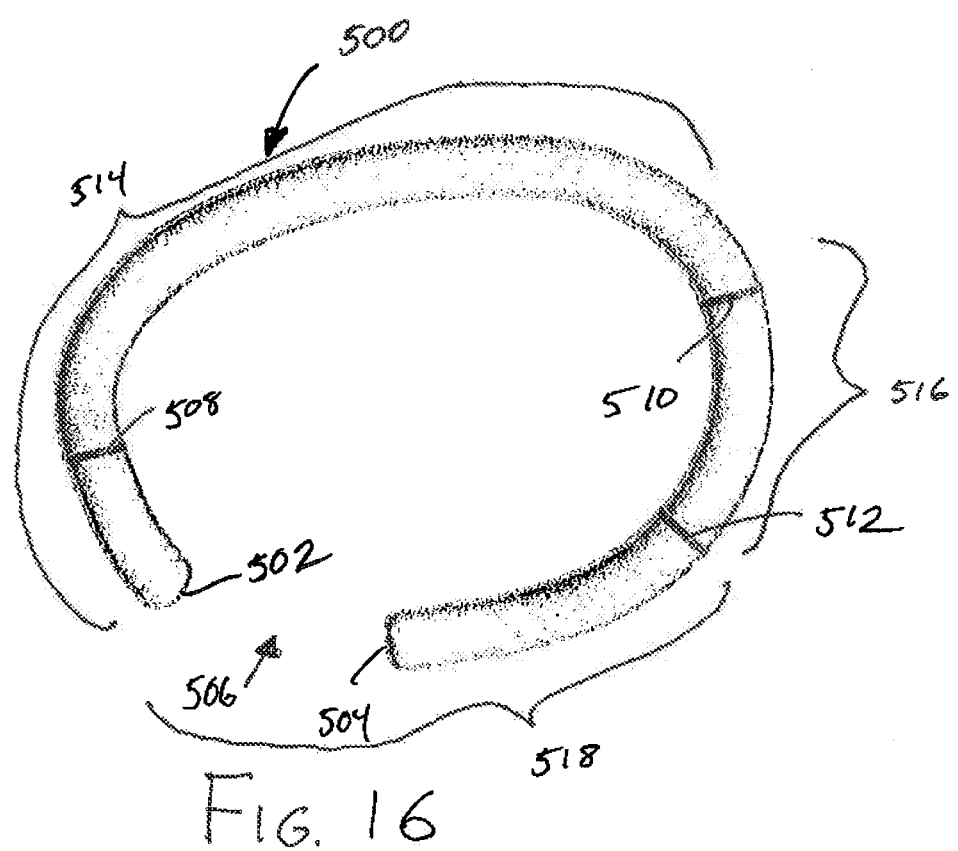
FIG. 16 is a top view of another exemplary annuloplasty band.

FIGS. 16-20 illustrate certain aspects of another annuloplasty device 500 for a tricuspid valve annulus in accordance with the present invention. As shown in FIG. 16, an open band includes a first end 502 and a second end 504 providing a gap 506 between the ends. A first marking 508 is preferably provided to indicate the anteroseptal commissure, a second marking 510 is preferably provided to indicate the anteroposterior commissure, and a third marking 512 is preferably provided to indicate the posteroseptal commissure. The distance between the markings 508 and 512 (including the gap 506) preferably relate directly to a measured distance between the anteroseptal commissure and the posteroseptal commissure, which distance is measured as the length of the septal aspect or leaflet of a tricuspid valve annulus. The length of the septal aspect of the annulus is considered to be a primary indicator of the size of the annulus for the purpose of determining the correct sizing of an annuloplasty device in accordance with the present invention and as discussed above. The position of the anteroposterior commissure and the related marking 510 is of less consideration, but can also be important. It may be the case that a properly fit annuloplasty device would be based upon the length of the septal aspect of a tricuspid annulus but with the marking 510 at a location to one side or the other of the anteroposterior commissure location. In this regard, it is also contemplated that the marking 510 could instead comprise either a series of similar or dissimilar markings or could comprise a shaded section of the band, or the like, to indicate a preferred range of where the location of the anteroposterior commissure should be located with a properly fitting annuloplasty device. Otherwise, FIG. 16 shows features similar to that of FIG. 2, discussed above, with an anterior portion that is designed to extend along the anterior aspect and then farther along the annulus past the anteroseptal commissure and a short distance along the septal aspect. As such, the first end 502 of the annuloplasty device 500 will be located along the septal aspect of a tricuspid annulus along with the second end 504, although separated from one another by the gap 506 to accommodate at least the AV node, as also discussed above. Like the embodiment discussed above with respect to FIG. 2, the annuloplasty device is noted as being divided into corresponding device portions including an anterior portion 514 (although an end portion thereof is intended to be implanted along a portion of a septal aspect of a tricuspid annulus), a posterior portion 516 and a septal portion 518.

Figure 17:
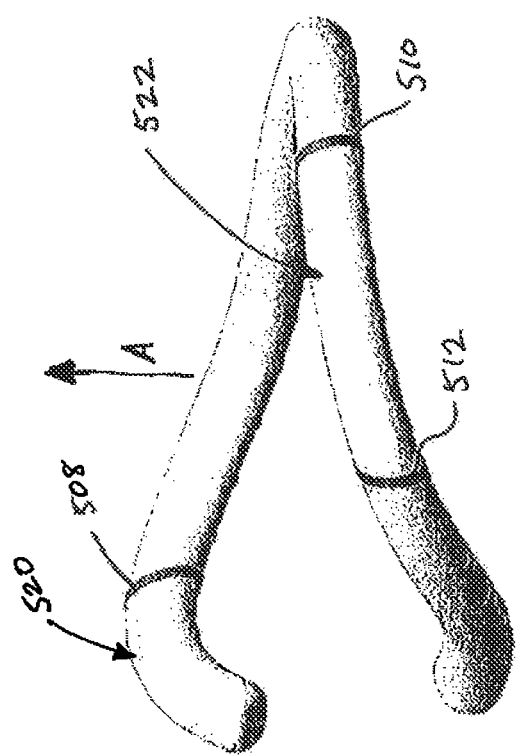
FIG. 17 is an isometric view of the exemplary annuloplasty band of FIG. 15.
Figure 18:
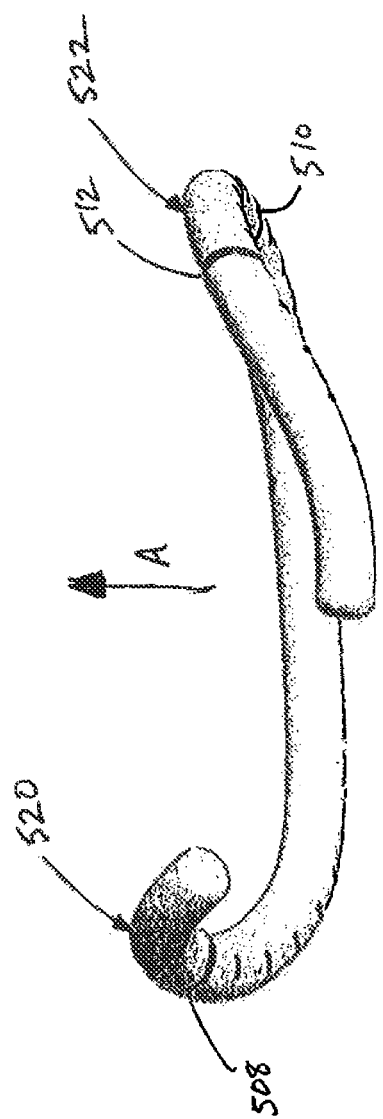
FIG. 18 is a side view of the exemplary annuloplasty band of FIG. 15.
Figure 19:
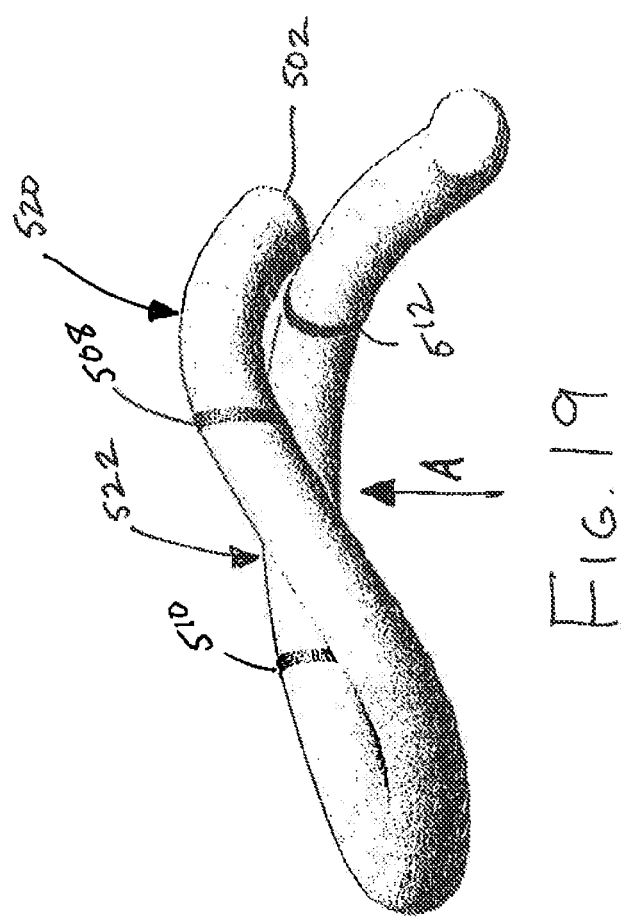
FIG. 19 is a view from anterior portion end of the exemplary annuloplasty band of FIG. 15.

In FIGS. 17, 18 and 19, an annuloplasty device 500 is shown from a right-side, front-side, and left-side views as having a curved nature in each of the three dimensions from end 502 to end 504. That is to say that the anterior portion 514, the posterior portion 516 and the septal portion 518 are each preferably curvilinear in each of the three dimensions. In this illustrated embodiment, a first curve 520 is provided along the anterior portion starting from the first end 502 in the superior direction (arrow A). This first curve 520 includes a peak that is preferably designed so as to be located near the anteroseptal commissure when implanted. Most preferably, the anteroseptal commissure is to be located at the marking 508 and the peak is slightly toward the first end 502 from the marking 508. The remainder of the anterior portion 514 preferably comprises a generally shallow inferior curvature that begins to curve again in the superior direction in approach to the posterior portion 516 of the annuloplasty device 500. A second curve 522 in the superior direction preferably lies primarily within the posterior portion 516. A portion of the second curve 522 preferably includes a peak that lies between the anteroposterior marking 510 and the posteroseptal marking 512. From a side view of the second curve 522, the marking 512 as implanted is most preferably designed to be implanted lower or more inferior than the marking 510 as implanted. As such, the posterior portion 516, as preferably designed between the markings 510 and 512, comprises a superior curve that is higher on one side (at the marking 510) than at the other side (at the marking 512), as the annuloplasty device is positioned at implant. Then, the septal portion 518 of the annuloplasty device 500 as extending from the posterior portion 516 generally comprises a gradual transition from the superior curvature of the second curve 522 to a slightly inferior curve that leads to the device second end 504.

The nature of the preferred curvature of the annuloplasty device 500 of FIGS. 16-19, with respect to the curves of the device in the superior and inferior directions, is illustrated in FIG. 20, which shows the device as if opened and laid out flat in a similar manner as in FIGS. 6 and 7. According to this preferred embodiment, the peak of the first curve 520 is designed to be higher, or more superior, than the peak of the second curve 522. It is, above, contemplated that the position of each peak of the curves 520 and 522 can vary along the length of the device and that the amplitudes of one or both likewise can vary. FIG. 20 also illustrates a preferred composition of the device 500 as comprising a stiffening element 524 that is coated by an elastomeric layer 526 and a sheath 528. The first end of the device includes an elastomeric extension portion 530 and the second end includes an elastomeric extension portion 532 that is of greater length than the first extension portion 530, such as discussed above, and can be made as extensions of the elastomeric coating layer 526.

The Example below describes how the shape and configuration (including location of the ends) of the device may be determined. Other methods are contemplated by the present invention, however.

EXAMPLE

Six sets of human heart data were analyzed in order to assess the shape of the tricuspid valve annulus. Datasets included one MRI dataset (MRI1) collected during systole and five CT datasets (CT1-CT5) collected during an arbitrary portion of the cardiac cycle. The data collected were composed into Digital Imaging and Communication in Medicine (DICOM) (available from Laurel Bridge Software, Inc., located in Newark, Del., U.S.A.) image files, which were then imported into Mimics® software (available from Materialise, located in Belgium). Utilizing the Mimics® software, left and right sides of the heart, in the images, were segmented by differentiating image contrast between the blood volume within the heart chambers and the heart tissue. The image pixels from the image were grouped (i.e., color coded) based on defining levels of image contrast below which all pixels with contrast less than the defined level were grouped (i.e., thresholding), with remaining pixels above the contrast level grouped separately. After thresholding, the tricuspid valve annulus was identified and the shape reconstructed, and other anatomical landmarks or features in the heart were identified.

Figure 11:
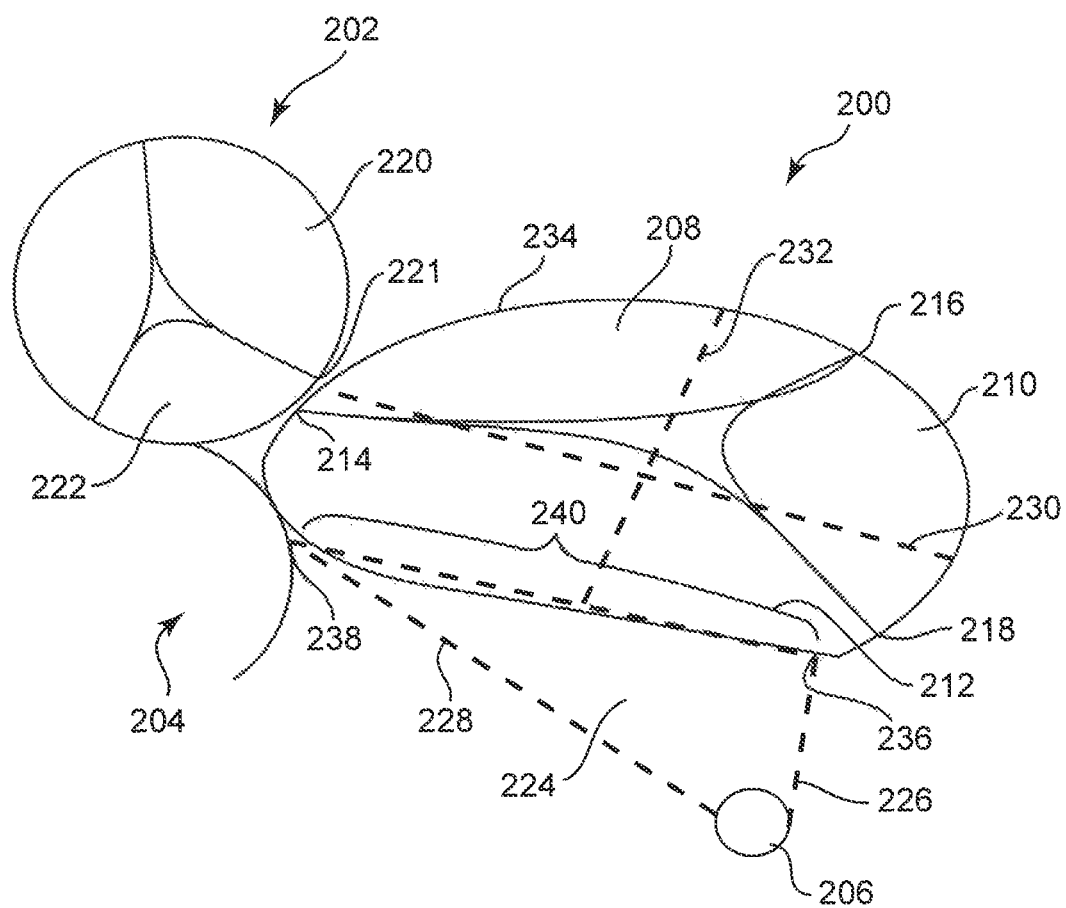
FIG. 11 is a schematic representation of the area of the heart near and including the tricuspid valve.

FIG. 11 is a schematic representation of the area of the heart near and including the tricuspid valve 200 from a superior perspective with respect to the annulus. The aortic valve 202 is schematically represented, as well as the membranous septum 204 of the heart, and the coronary sinus 206. The anterior 208, posterior 210 and septal 212 leaflets, and the anteroseptal 214, anteroposterior 216 and posteroseptal 218 commissures of the tricuspid valve 200 are also illustrated. Also, the right coronary cusp 220 and the non-coronary cusp 222 of the aortic valve 202 are shown. Between the two cusps is the right coronary/non-coronary commissure 221.

Figure 12:
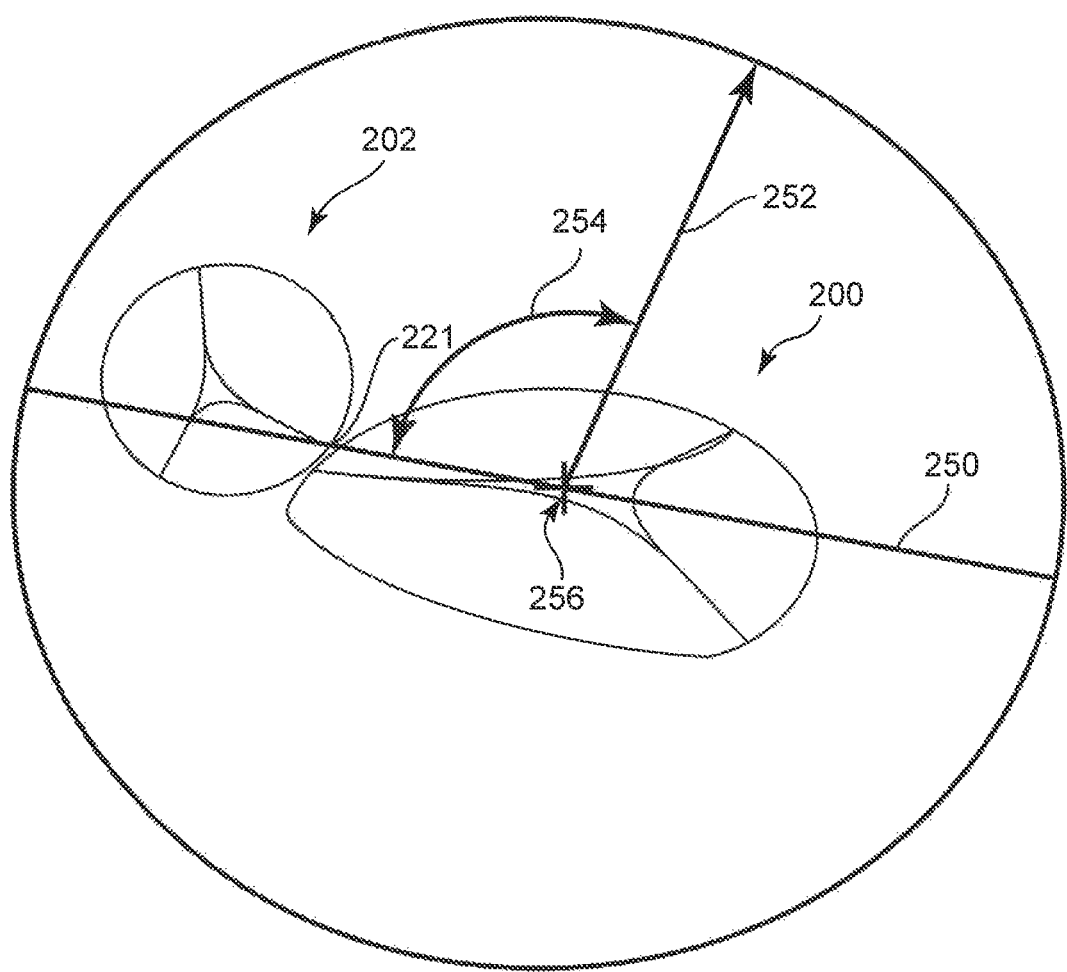
FIG. 12 is the schematic representation of FIG. 11 with lines demonstrating how the cylindrical coordinate system was established with regard to the tricuspid annulus.

Axes and other boundaries were constructed, as shown on FIG. 12, from anatomical landmarks in the heart, which were used in the analysis of the six datasets. A major axis 230 and a minor axis 232 of the tricuspid valve 200 were determined. Also, the Triangle of Koch (TOK) 224 was determined. The TOK height 226 (or base of triangle) extends between the coronary sinus orifice 206 and a point 236 normal to the coronary sinus orifice 102 along the septal aspect of the tricuspid annulus 234. The TOK length 228 (one side of triangle) extends between the coronary sinus orifice 206 and the location 238 where the septum 204 and the tricuspid valve 200 come together, and extends along the Tendon of Todaro of the heart. The second side of the triangle extends along the septal aspect of the annulus generally.

In the analysis, the tricuspid valve annulus 234 was identified by selecting two points on the annulus 234 in each image slice for image planes passing obliquely through the annulus, allowing for generation of an interpolated curve through the data points. Additionally, curves were generated for the aortic valve commissures, the coronary sinus orifice 206, and the TOK 224, which provided anatomic references or landmarks with respect to the tricuspid valve annulus.

From the reconstructed anatomic references or landmarks, measurements were made using the Mimics® software for each dataset, in order to categorize the annulus shape. The measurements included the major axis 230 and minor axis 232 dimensions of the valve annulus, the full annular perimeter, the partial annular perimeter 240 (clockwise perimeter with respect to the annulus region bounded by the TOK 224), TOK height 226, and TOK length 228. In addition to the measured values, ratios were computed for the minor-to-major axis diameters and the partial-to-full perimeters to assess the degree of annular circularity and the percentage of the annular perimeter adjacent to the conductive tissue along the septal aspect of the annulus. Tables 1 and 2 below provide measurements and averages, standard deviations, maxima and minima for the 5 CT datasets (CT1-CT5) and the 1 MRI dataset (MRI1).

TABLE 1

Measurements made in Mimics® software for each of the six datasets.

| Case | Full Perimeter (mm) | Partial Perimeter (mm) | Major (mm) | Minor (mm) | TOK H (mm) | TOK L (mm) |
|---|---|---|---|---|---|---|
| CT1 | 102.48 | 75.79 | 35.89 | 23.79 | 6.86 | 26.69 |
| CT2 | 104.77 | 85.52 | 32.68 | 31.57 | 6.06 | 19.25 |
| CT3 | 120.54 | 103.01 | 42.60 | 35.23 | 6.19 | 17.53 |
| CT4 | 127.96 | 110.89 | 41.80 | 39.33 | 12.90 | 17.07 |
| CT5 | 135.97 | 111.45 | 43.32 | 37.22 | 12.87 | 24.52 |
| MRI1 | 147.26 | 126.02 | 49.19 | 42.99 | 14.29 | 21.24 |
| Average | 123.16 | 102.11 | 40.91 | 35.02 | 9.86 | 21.05 |
| STD | 17.55 | 18.47 | 5.85 | 6.71 | 3.87 | 3.88 |
| Max | 147.26 | 126.02 | 49.19 | 42.99 | 14.29 | 26.69 |
| Min | 102.48 | 75.79 | 32.68 | 23.79 | 6.06 | 17.07 |

TABLE 2

Ratios computed from minor/major axis dimensions and partial/full perimeters.

| Case | Minor:Major Axis Ratio | Partial:Full Perimeter Ratio |
|---|---|---|
| CT1 | 0.66 | 0.74 |
| CT2 | 0.97 | 0.82 |

TABLE 2-continued

Ratios computed from minor/major axis dimensions and partial/full perimeters.

| Case | Minor:Major Axis Ratio | Partial:Full Perimeter Ratio |
|---|---|---|
| CT3 | 0.83 | 0.85 |
| CT4 | 0.94 | 0.87 |
| CT5 | 0.86 | 0.82 |
| MRI1 | 0.87 | 0.86 |
| Average | 0.85 | 0.83 |
| STD | 0.12 | 0.05 |
| Max | 0.97 | 0.87 |
| Min | 0.66 | 0.74 |

The curves generated for the tricuspid annulus, the aortic commissures, and coronary sinus orifice were outputted from the Mimics® software as 3D points in Cartesian coordinate format, with the coordinate system referenced to MRI and CT scanners that were used. Using DPlot software (available from HydeSoft Computing, LLC, located in Vicksburg, Miss., U.S.A.), a plane was computed for the tricuspid annulus points in 3D space using a least squares based algorithm. From the DPlot computed plane, residual offset (vertical offset) of each point from the plane was computed to assess the non-planarity of the annulus, with the maximum residual offset (positive direction), minimum residual offset (negative direction), and residual offset range computed for each dataset. Table 3 provides the residual offset maxima, minima and ranges for each dataset, and also provides the averages, standard deviations, maxima and minima.

TABLE 3

Residual offsets of tricuspid annulus data points from DPlot computed plane for each dataset.

| Case | Residual Offset Max (mm) | Residual Offset Min (mm) | Residual Offset Range (mm) |
|---|---|---|---|
| CT1 | 2.79 | −4.00 | 6.78 |
| CT2 | 6.79 | −6.19 | 12.98 |
| CT3 | 4.90 | −4.77 | 9.67 |
| CT4 | 12.70 | −9.95 | 22.65 |
| CT5 | 4.27 | −5.40 | 9.67 |
| MRI1 | 4.58 | −4.82 | 9.40 |
| Average | 6.00 | −5.85 | 11.86 |
| STD | 3.52 | 2.14 | 5.64 |
| Max | 12.70 | −4.00 | 22.65 |
| Min | 2.79 | −9.95 | 6.78 |

To assess the normal distance of each tricuspid annulus point from a computed plane, the annulus curves for each dataset were loaded into Pro/ENGINEER (available from Parametric Technology Corporation, located in Needham, Mass., U.S.A.). The computed plane from D-Plot was duplicated in Pro/ENGINEER using the coefficients of the plane equation computed from D-Plot. A Cartesian coordinate system was then defined in Pro/ENGINEER, with the z-axis normal to the computed plane, and the x and y axes contained within the plane. The coordinate data of annulus points with respect to the newly defined coordinate system were outputted to Excel (available from Microsoft Corporation, located in Redmond, Wash., U.S.A.) to determine the normal distance (z-coordinate) of the points with respect to the Pro/ENGINEER computed plane, with maximum, minimum, and range reported.

Finally, to locate maximum and minimum z-coordinate points in 3D space, a local cylindrical coordinate system $(r,\theta,z)$ was defined for each dataset separately. FIG. 12 is a schematic representation showing how the cylindrical coordinate system was defined with regard to the schematic representation of FIG. 11, in order to locate maximum and minimum z-coordinates along the tricuspid annulus. Center point 256 is the centroid of the annulus coordinates in x and y. The line 250 though the center point 256 (diameter of the circle) is an axis through the center point 256 and the peak 221 of the right coronary/non-coronary aortic valve commissure. The line 252 is showing a radius (r) and the line 254 is showing the positive angular direction ($\theta$) (clockwise) from the line 250 to the line 252. The plane of the drawing in FIG. 12 is the $\theta$ plane, with the z-axis extending normal to the drawing. The curves for the aortic valve and tricuspid annulus were loaded into Pro/ENGINEER for the analysis. The center point 256 for the coordinate system was defined by centering the x-y Cartesian coordinates of the annulus points such that the average of difference of individual x and y coordinates from the average x and y coordinates equals zero. Using the computed plane originally defined for the tricuspid annulus, axes were defined normal to the plane vertically through the center point of the annulus, and through the center point and the peak point of the aortic valve commissure between the right coronary non-coronary cusps. First, the magnitude and angular position of the maximum and minimum z-coordinates within each dataset were located (Max 1 and Min 1, in Table 4). Second, the datasets were truncated or excluded from the center point of the tricuspid valve annulus toward the aortic valve side of the annulus, and the magnitude and angular position of the second maximum and minimum z-coordinates were located (Max 2 and Min 2, in Table 4).

TABLE 4

$1^{st}$ and $2^{nd}$ maximum and minimum z-coordinates for each dataset along with angular position in cylindrical coordinate system.

| | Max1 | | Max 2 | | Min1 | | Min2 | |
|---|---|---|---|---|---|---|---|---|
| Case | z (mm) | θ Position (deg) | z (mm) | θ Position (deg) | z (mm) | θ Position (deg) | z (mm) | θ Position (deg) |
| CT1 | 1.4 | −109.5 | 1.2 | 112.8 | −2.0 | 182.9 | −0.9 | 329.9 |
| CT2 | 1.9 | 7.2 | 0.9 | 124.5 | −1.8 | 56.6 | −1.6 | 254.7 |
| CT3 | 2.1 | −78.1 | 1.4 | 213.0 | −2.1 | 21.8 | −1.4 | 86.8 |
| CT4 | 2.6 | 10.2 | 1.0 | 158.6 | −2.0 | 247.0 | −1.0 | 55.2 |
| CT5 | 1.6 | −26.7 | 1.8 | 185.4 | −2.2 | 267.2 | −1.6 | 110.0 |
| MRI1 | 3.9 | −82.7 | 1.6 | 129.9 | −3.7 | 255.1 | −3.0 | 57.1 |
| Average | 2.3 | −46.6 | 1.3 | 154.0 | −2.3 | 171.8 | −1.6 | 149.0 |
| STD | 0.9 | 50.5 | 0.3 | 39.1 | 0.7 | 107.3 | 0.8 | 115.3 |
| Max | 3.9 | 10.2 | 1.8 | 213.0 | −1.8 | 267.2 | −0.9 | 329.9 |
| Min | 1.4 | −109.5 | 0.9 | 112.8 | −3.7 | 21.8 | −3.0 | 55.2 |
| Range | 2.5 | 119.7 | 0.8 | 100.2 | 1.9 | 245.4 | 2.1 | 274.6 |

From analysis of the data, general trends were observed. The ratio of the minor-to-major axis diameters showed that the annuli were non-circular for the cases analyzed, with a maximum ratio of 0.97, a minimum of 0.66, and an average value of 0.85. The partial:full perimeter ratios showed a maximum of 0.87, and minimum of 0.74, and an average of 0.83, indicating that the conductive tissue region makes up approximately 17% of the annular perimeter. The residual offset data indicated clearly that the annulus is non-planar, with the average maximum and minimum approximately 6 mm and the range approximately 12 mm. The maximum and minimum z-coordinate data indicated average normal offsets of Max 1 and Min 1 data points from the computed plane of approximately 2.3 mm, with Max 2 and Min 2 offset by 1.3 and 1.6 mm, respectively. By locating the positions of the maximum and minimum z-coordinates, the results showed the largest positive z-coordinate along the annulus was generally located near the aortic valve, counterclockwise from the right coronary/non-coronary commissure. The results also showed a general rise of the annular points in the positive z direction (direction superior to the computed plane) from the septal and anterior aspects of annulus toward the aortic valve for some datasets (particularly MRI1). This result suggests a saddle-shaped annulus.

Based on the analysis of the six datasets, the tricuspid valve annulus can be defined as a non-circular and non-planar shaped tissue structure, with a general relationship of minimum points along the septal and anterior aspects of the annulus and a rise up to a maximum height near the right coronary/non-coronary commissure of the aortic valve. These data suggest a distinct relationship between the tricuspid valve and the aortic valve, where the shape of the tricuspid valve near its interaction with the aortic valve may facilitate appropriate aortic valve function. Therefore, surgical repair procedures of the tricuspid valve should attempt to maintain this distinct relationship to both restore tricuspid valve function and maintain proper aortic valve function. In addition to this relationship, a consistent relationship was observed across the datasets for the TOK, indicating that the conductive tissue region of the heart near the tricuspid annulus makes up approximately 17% of the tricuspid annulus perimeter. This provides a reference point for appropriate termination of surgical repair of the tricuspid annulus along the septal annulus to avoid damage to the conductive tissue. General ranges for the preferred shape/design of a tricuspid valve annuloplasty device are defined in Table 5 below (based on averages of above data, plus or minus one standard deviation).

TABLE 5

General ranges for shape/design of a tricuspid valve annuloplasty device.

| | Range |
|---|---|
| 2D (Short Axis) Shape - Minor:Major Ratio | 0.75-0.96 |
| Percentage of Device Perimeter to Exclude Along Septal Aspect of Annulus to Avoid Conductive Tissue | 12-22% |
| Residual (Vertical) Offset Range of Maximum and Minimum Points from Computed Plane Through Device | 6.2-17.5 mm |
| Normal Offset of Maximum and Minimum Points from Computed Plane Through Device | −3 to +3 mm |
| Angular Position of Maximum Normal Offset With Respect to Axis Through Center Point of Device and Point on Device Closest to Right Coronary/Non-coronary Commissure | −100 to 0 degrees |

It is to be understood that while particular embodiments of the present inventive annuloplasty device have been illustrated for use in typical valve repair procedures, various modifications to shape, and arrangement of parts can be made as may be desirable for varying applications as may relate to valve sizes, disease states, or later developed techniques.

The present invention has now been described with reference to several embodiments thereof. The entire disclosure of any article, patent or patent application identified herein is hereby incorporated by reference. The foregoing detailed description has been given for clarity of understanding only. No unnecessary limitations are to be understood therefrom. It will be apparent to those skilled in the art that many changes can be made in the embodiments described without departing from the scope of the invention.

The invention claimed is:

1. An annuloplasty device for implantation adjacent an annulus of a tricuspid valve, the annulus comprising anterior, posterior and septal aspects adjacent anterior, posterior and septal leaflets, respectively, of the tricuspid valve, the device comprising:
a band comprising:
opposing, first and second free ends;
an anterior portion, a posterior portion and a septal portion shaped to conform to, and for implantation adjacent, the anterior, posterior and septal aspects of the annulus, respectively, wherein the band is curvilinear, with substantially no flat portions along at least the anterior portion in any of three dimensions, and forming a shape; and
first, second, and third markings configured to indicate proper placement of the band adjacent the annulus, wherein the first marking is configured for placement adjacent an anteroseptal commissure of the tricuspid valve, the second marking is configured for placement adjacent an anteroposterior commissure of the tricuspid valve, and the third marking is configured for placement adjacent a posteroseptal commissure of the tricuspid valve.

2. The annuloplasty device of claim 1, wherein the annuloplasty device is configured to effect a reduction of the septal aspect of the annulus.

3. The annuloplasty device of claim 2, wherein the amount of reduction of the septal aspect can be greater than about 25% and up to about 33%.

4. The annuloplasty device of claim 1, wherein the curvilinear shape includes varying slope between four slope minima.

5. The annuloplasty device of claim 1, wherein a path from the first free end to the second free end includes at least two maximum and two minimum positions along the path.

6. The annuloplasty device of claim 1, wherein the band further comprises:
a sheath; and
a stiffening element disposed within the sheath.

7. The annuloplasty device of claim 6, wherein the stiffening element comprises a diameter that is reduced towards opposing, first and second ends of the stiffening element.

8. The annuloplasty device of claim 1, wherein the band further defines a first end portion including the first free end and a second end portion including the second free end, and further wherein the first and second end portions of the band comprise a flexible material.

9. The annuloplasty device of claim 1, wherein the band further comprises opposing, first and second sides, wherein the band has a curvilinear shape in continuous extension from the first free end to the second free end, the curvilinear shape defining a path having a first curve in a direction of the first side adjacent the first free end, a second curve in a direction of the second side between the first curve and the second free end, a third curve in a direction of the first side between the second curve and the second free end, and a fourth curve in a direction of the second side between the third curve and the second free end.

10. The annuloplasty device of claim 1, wherein the band is configured such that when the device is implanted, the first free end will be located near a junction of the septal and anterior aspects of the annulus and the second free end will be located near the septal aspect of the annulus.

* * * * *